US007125971B2

(12) United States Patent
Maoka et al.

(10) Patent No.: US 7,125,971 B2
(45) Date of Patent: Oct. 24, 2006

(54) FULL-LENGTH GENOMIC RNA OF PAPAYA LEAF-DISTORTION MOSAIC VIRUS

(75) Inventors: Tetsuo Maoka, Hokkaido (JP); Tatsuji Hataya, Hokkaido (JP)

(73) Assignee: Japan International Research Center For Agricultural Sciences, Ibaraki (JP)

( * ) Notice: Subject to any disclaimer, the term of this patent is extended or adjusted under 35 U.S.C. 154(b) by 769 days.

(21) Appl. No.: 10/076,839

(22) Filed: Feb. 15, 2002

(65) Prior Publication Data

US 2005/0158707 A1 Jul. 21, 2005

(30) Foreign Application Priority Data

Feb. 16, 2001 (JP) ............................ 2001-040523

(51) Int. Cl.
*C07H 21/02* (2006.01)
*C07H 21/04* (2006.01)

(52) U.S. Cl. .................................................... 536/23.1

(58) Field of Classification Search ................ 536/23.1
See application file for complete search history.

(56) References Cited

U.S. PATENT DOCUMENTS 5,859,224 A * 1/1999 Maoka et al. ............ 536/23.72

OTHER PUBLICATIONS

Sequence alignment of SEQ ID No.: 1 with Genseq database accession No.: AB088221 of Maoki et al. in (Archives of Virology. 1996; 141 (1): 197-204).*
Maoka et al. in (Archives of Virology. 1996; 141 (1): 197-204).*
Japanese Journal of Tropical Agriculture, vol. 45, Extra Issue 1, Mar. 30/31, 2001, pp. 93-94.
Japan International Research Center for Agricultural Services (JIRCAS) Newsletter, No. 29, Dec. 2001, p. 5.

* cited by examiner

*Primary Examiner*—Bruce R. Cambell
*Assistant Examiner*—Myron G. Hill
(74) *Attorney, Agent, or Firm*—Davidson, Davidson, Kappel, LLC

(57) ABSTRACT

The purpose of the present invention is to determine the nucleotide sequence of the full-length genomic RNA of papaya leaf-distortion mosaic virus. The present invention provides the full-length genomic RNA of papaya leaf-distortion mosaic virus, a method for diagnosing infection with papaya leaf-distortion mosaic virus using the full-length genomic RNA, a method for producing a papaya leaf-distortion mosaic virus-resistant plant, and a method for producing a foreign protein in a plant body.

2 Claims, 8 Drawing Sheets

BLASTN 2.2.1 [Apr-13-2001]

Reference:
Altschul, Stephen F., Thomas L. Madden, Alejandro A. Sch?ffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.

RID: 1009527356-10099-15388

Query=
(1440 letters)

Database: All GenBank+EMBL+DDBJ+PDB sequences (but no EST, STS, GSS, or phase 0, 1 or 2 HTGS sequences).
1,073,652 sequences; 4,829,212,789 total letters If you have any problems or questions with the results of this search please refer to the BLAST FAQs Taxonomy reports Distribution of 19 Blast Hits on the Query Sequence

| | Sequences producing significant alignments: | Score (bits) | E Value |
|---|---|---|---|
| 1 | gi\|9628890\|ref\|NC_001723.1\| Peanut stripe virus, complete g... | 68 | 2e-08 |
| 2 | gi\|1016234\|gb\|U34972.1\|PSU34972 Peanut stripe virus mRNA po... | 68 | 2e-08 |
| 3 | gi\|1335723\|gb\|U05771.1\|PSU05771 Peanut stripe virus, comple... | 68 | 2e-08 |
| 4 | gi\|15642775\|ref\|NC_000853.1\| Thermotoga maritima, complete ... | 44 | 0.36 |
| 5 | gi\|4980775\|gb\|AE001710.1\|AE001710 Thermotoga maritima secti... | 44 | 0.36 |
| 6 | gi\|16973823\|emb\|AL354976.11\|AL354976 Human DNA sequence fro... | 42 | 1.4 |
| 7 | gi\|7838255\|emb\|AL132822.15\|HSJ1017F8 Human DNA sequence fro... | 42 | 1.4 |
| 8 | gi\|15341592\|gb\|AC018499.3\| Homo sapiens chromosome 3 clone ... | 40 | 5.6 |
| 9 | gi\|14589685\|gb\|AC008167.5\| Homo sapiens BAC clone RP11-1720... | 40 | 5.6 |
| 10 | gi\|16445165\|gb\|AC092038.3\| Homo sapiens chromosome 3 clone ... | 40 | 5.6 |
| 11 | gi\|15020311\|gb\|AY040316.1\| Hylurdrectonus araucariae elonga... | 40 | 5.6 |
| 12 | gi\|14670056\|gb\|AC073614.17\|AC073614 Homo sapiens Xp BAC RP1... | 40 | 5.6 |

Fig.1a

| Sequence | Alignment Score |
|---|---|
| 1-3 | 50-80 |
| 4-12 | 40-50 |

BLASTN 2.2.1 [Apr-13-2001]

Reference:
Altschul, Stephen F., Thomas L. Madden, Alejandro A. Sch?ffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.

RID: 1010120805-18751-22816

Query=
(882 letters)

Database: All GenBank+EMBL+DDBJ+PDB sequences (but no EST, STS, GSS, or phase 0, 1 or 2 HTGS sequences).
1,079,316 sequences; 4,832,507,720 total letters If you have any problems or questions with the results of this search please refer to the BLAST FAQs Taxonomy reports Distribution of 143 Blast Hits on the Query Sequence

Fig.2a

BLASTN 2.2.1 [Apr-13-2001]

Reference:
Altschul, Stephen F., Thomas L. Madden, Alejandro A. Sch?ffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.

RID: 1010127418-14473-18661

Query=
(1374 letters)

Database: All GenBank+EMBL+DDBJ+PDB sequences (but no EST, STS, GSS, or phase 0, 1 or 2 HTGS sequences).
1,079,316 sequences; 4,832,507,720 total letters If you have any problems or questions with the results of this search please refer to the BLAST FAQs Taxonomy reports Distribution of 99 Blast Hits on the Query Sequence

Fig.3a

BLASTN 2.2.1 [Apr-13-2001]

Reference:
Altschul, Stephen F., Thomas L. Madden, Alejandro A. Sch?ffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.

RID: 1010128690-26317-13567

Query=
(1563 letters)

Database: All GenBank+EMBL+DDBJ+PDB sequences (but no EST, STS, GSS, or phase 0, 1 or 2 HTGS sequences).
1,079,316 sequences; 4,832,507,720 total letters If you have any problems or questions with the results of this search please refer to the BLAST FAQs Taxonomy reports Distribution of 175 Blast Hits on the Query Sequence

Fig.4a

FULL-LENGTH GENOMIC RNA OF PAPAYA LEAF-DISTORTION MOSAIC VIRUS

BACKGROUND OF THE INVENTION

1. Field of the Invention

The present invention relates to the full-length genomic RNA of papaya leaf-distortion mosaic virus.

2. Description of the Related Art

A problem of a disease called papaya leaf-distortion mosaic disease has arisen in papaya plants in Subtropic areas, causing mosaic symptoms on leaves and ring spots on fruits. It has been shown that this disease is caused by infection with a papaya leaf-distortion mosaic virus (hereinafter referred to as "PLDMV"). PLDMV belonging to the genus Potyvirus of the family Potyviridae is in a string-like shape, and is approximately 800 nanometers in length. The virus is transmitted nonpersistently by aphids. Viral components include its genome consisting of RNA and periplastic proteins surrounding the RNA. The RNA genes contain nucleotide sequences encoding 10 types of proteins required for infection and replication: P1, HC-Pro, P3, 6K1, CI, 6K2, NIa-VPg, NIa-Pro, NIb and CP.

Of these 10 types of proteins encoded by PLDMV genes; only the CP region encoding a periplastic protein has been analyzed so far. No other regions have been analyzed and none of the nucleotide sequences of these regions have been reported.

SUMMARY OF THE INVENTION

The use of the nucleotide sequence of the full-length genomic RNA in addition to the CP region would be very useful in elucidating the functions and roles of PLDMV. Accordingly, the object of the present invention is to determine the nucleotide sequence of the full-length genomic RNA of PLDMV.

To solve the problems, we have determined the full-length nucleotide sequence by cDNA cloning for the entire gene region of PLDMV. Then, we have completed the invention by elucidating the gene structure of regions encoding various proteins from the nucleotide sequence.

Accordingly, the present invention relates to an RNA and a DNA, each of which comprises a nucleotide sequence as shown in SEQ ID NO: 1 (or a nucleotide sequence complementary to said nucleotide sequence), or a nucleotide sequence as shown in SEQ ID NO: 1 in which uracil is replaced by thymine(or a nucleotide sequence complementary to said nucleotide sequence), respectively.

The present invention further relates to a method for diagnosing infection with PLDMV in a plant, comprising determing whether the plant is infected with the virus by detecting an RNA fragment specific in the virus from the plant, wherein the RNA fragment corresponds to a part of a nucleotide sequence as shown in SEQ ID NO: 1.

The present invention further relates to a method for producing a PLDMV-resistant plant, comprising integrating a DNA fragment having a function to impart resistance against PLDMV into the plant, wherein the DNA fragment corresponds to a part of a nucleotide sequence as shown in SEQ ID NO: 1.

The present invention further relates to a method for producing a foreign protein in a plant comprising the steps of:

1) synthesizing cDNA from genomic RNA of PLDMV;
2) adding a nucleotide sequence encoding an amino acid sequence, which can be cleaved with protease derived from PLDMV, to the 5' terminus and the 3' terminus of a gene encoding said foreign protein to obtain a DNA fragment having the nucleotide sequence and a nucleotide sequence of the gene;
3) inserting the DNA fragment of 2) into the cDNA of 1);
4) preparing an RNA by allowing an RNA polymerase to act on the cDNA of 3); and
5) infecting a plant with the RNA of 4).

The present invention further relates to a protein selected from the group consisting of the following (a) to (c), and DNAs encoding them:

(a) a protein comprising an amino acid sequence as shown in SEQ ID NO: 4;
(b) a protein comprising an amino acid sequence as shown in SEQ ID NO: 4 having deletion, substitution, or addition of one or more amino acids, and having a protease activity to cleave peptide bonds between Gln-Ala, Gln-Ser, and Glu-Gly; and
(c) a protein derived from PLDMV encoded by a DNA which hybridizes to a DNA comprising a nucleotide sequence as shown in SEQ ID NO: 3 or a DNA complementary to said nucleotide sequence under stringent conditions, and having a protease activity to cleave peptide bonds between Gln-Ala, Gln-Ser, and Glu-Gly.

This specification includes part or all of the contents as disclosed in the specification and/or drawings of Japanese Patent Application No. 2001-40523, which is a priority document of the present application.

DETAILED DESCRIPTION OF THE INVENTION

Hereinafter, the present invention will be described in detail.

(1) RNA and DNA

RNA and DNA of the present invention relate to the full-length genomic RNA of papaya leaf-distortion mosaic virus("PLDMV"), and each of them comprises a nucleotide sequence as shown in SEQ ID NO: 1 (or a nucleotide sequence complementary to said nucleotide sequences), or a nucleotide sequence as shown in SEQ ID NO: 1 in which uracil is replaced by thymine (or a nucleotide sequence complementary to said nucleotide sequences), respectively.

DNA of the invention can be obtained from a cDNA library that is synthesized from the viral RNA, or directly from the viral RNA by the RT-PCR method, using appropriate primers which is prepared based on the genetic information shown in SEQ ID NO: 1.

Alternatively, if the information is not used, the DNA of the invention can be obtained, for example, by the following method we have carried out, with modification as needed.

Firstly, viral particles are isolated and purified from leaves of PLDMV-infected *Cucumis metuliferus*, and then an RNA is extracted from the particles. Using the RNA as a template, cDNA is synthesized with oligo dT primers. The resulting cDNA is incorporated into a phagemide vector pT7Blue for transformation of *E. coli*, and thereby obtaining a cDNA library. Then, PCR is performed using the transformed *E. coli* as a template so as to examine the presence or absence of inserts, and select plasmids containing the cDNA which contains PLDMV gene. Next, the cDNA obtained as described above are cloned. Using the cloned plasmids, nucleotide sequences of the cDNA can be determined by the method, such as dideoxy method. Of the obtained nucleotide sequences, a sequence closest to 5' end of the cDNA is used to prepare a primer. Repetition of the above-mentioned steps can yield a more upstream nucleotide sequence.

RNA of the present invention can be obtained by transcribing the DNA of this invention.

The DNA and RNA of the invention can be used for the diagnosis of infection with PLDMV, production of a PLDMV-resistant plant, and production of a foreign protein in a plant, as described below.

(2) Diagnosing Infection with PLDMV in a Plant

A method of the invention for diagnosing infection with PLDMV is a method which comprises determing whether the plant is infected with the virus by detecting an RNA fragment specific in the virus from the plant, wherein the RNA fragment corresponds to apart of a nucleotide sequence as shown in SEQ ID NO: 1.

"an RNA fragment corresponds to a part of the nucleotide sequence as shown in SEQ ID NO: 1" as used herein means:

① the RNA fragment comprises a nucleotide sequence which is identical to a part of a nucleotide sequence as shown in SEQ ID NO: 1;

② the RNA fragment comprises a nucleotide sequence which is complementary to a part of a nucleotide sequence as shown in SEQ ID NO: 1;

③ the RNA fragment is that of ① or ②, having deletion, substitution, or addition of one or more nucleotides, and having species-specificity sufficient to use it as an index in diagnosing infection with PLDMV.

An RNA fragment to be detected may correspond to any region of a nucleotide sequence as shown in SEQ ID NO: 1, the RNA fragment corresponding to P1 protein-coding region with high species-specificity is preferred. The P1 protein-coding region corresponds to a part of the sequence of the nucleotides 136–1575 as shown in SEQ ID NO: 1. It is demonstrated by BLASTN homology search that the region corresponding to the nucleotides 1–150 and the region corresponding to the nucleotides 1200–1440 of the P1 protein-coding region have high species-specificity, as shown in FIG. 1. Thus, the RNA fragments correspond to the nucleotides 1–150 of the P1 protein-coding region and the RNA fragments correspond to the nucleotides 1200–1440 of the P1 protein-coding region are highly preferred.

A method for detecting an RNA fragment includes, but is not limited to, hybridization method using a labeled DNA or RNA as a probe, and RT-PCR method.

(3) A Method for Producing a PLDMV-Resistant Plant

A method for producing a PLDMV-resistant plant of the invention comprises integrating a DNA fragment having a function to impart resistance against PLDMV into a plant, wherein the DNA fragment corresponds to a part of a nucleotide sequence as shown in SEQ ID NO: 1.

"DNA fragment corresponds to a part of a nucleotide sequence as shown in SEQ ID NO: 1" as used herein means:

① the DNA fragment comprises a nucleotide sequence which is identical to a part of a nucleotide sequence as shown in SEQ ID NO: 1 in which uracil is replaced by thymine;

② the DNA fragment comprises a nucleotide sequence which is complementary to a part of a nucleotide sequence as shown in SEQ ID NO: 1 in which uracil is replaced by thymine; and ③ the DNA fragment is that of ① or ②, having deletion, substitution, or addition of one or more nucleotides, and having a function to impart resistance against PLDMV to the plant.

Tennant et al. have reported that they have succeeded in imparting virus resistance to a plant by integrating a region encoding a periplastic protein of papaya ringspot virus type P into the plant (Tennant et al., Phytopathology 84: 1359–1366, 1994). Maiti et al. have reported that they were able to impart virus resistance to a plant by integrating a region encoding a HC-Pro protein of tobacco vein mottling virus into the plant (Maiti, I. B., Murphy, J. F., Shaw, J. G., Hunt, A., 1993, Proc. Narl. Acad. Sci. USA. 90: 6110–6114). Further, Audy et al have reported that they were able to impart virus resistance to a plant by integrating a region encoding an NIb protein of potato virus Y into the plant (Audy, P., Palukaitis, P., Slack, S. A., Zaitlin, M., 1994, Molecular Plant-Microbe Inerractions 7: 15–22). Therefore, a preferable DNA fragment to be integrated into a plant corresponds to a part or whole of regions, including a capsid protein (CP) coding region (nucleotides 9064–9945 as shown in SEQ ID NO: 1), a HC-Pro coding region (nucleotides 1576–2949), and/or a NIb coding region (nucleotides 7501–9063). Furthermore, the part of these regions, including the regions corresponding to the nucleotides 1–380 and the nucleotides 780–882 of capsid protein (CP), the regions corresponding to the nucleotides 27–140 and the nucleotides 1280–1374 of a HC-Pro coding region, and/or the regions corresponding to the nucleotides 1–81 and the nucleotides 1447–1563 of a NIb coding region have high species-specificity. The results of BLASTN homology search are shown in FIGS. 2–4. Therefore, the DNA fragments correspond to these regions are more preferable.

A PLDMV resistant plant can be produced by integrating a DNA fragment corresponding to a part of a nucleotide sequence as shown in SEQ ID NO: 1 into a plant cell with appropriate promoter and terminator sequences, and allowing the plant cell to regenerate to a plant body. A preferable plant cell, to which the DNA fragment is introduced, is derived from a PLDMV-infectious plant, including papaya, cucumber, *Cucumis melo* var. conomon, and *Cucumis metuliferus*. Examples of a form of the plant cell include, but are not specifically limited to, cultured cells, protoplasts, callus, slices of a leaf, embryos. Examples of a promoter sequence used herein include a 35S promoter of cauliflower mosaic virus, and an alcohol dehydrogenase 1 gene promoter. Examples of a terminator sequence used herein include a NOS terminator, and an alcohol dehydrogenase 1 gene terminator. Introduction of the DNA into the plant cell can be performed by various methods known to the skilled in the art. Examples of such a method include methods which use *Agrobacterium tumefaciens, Agrobacterium rhizogenes* and the like an electroporation method, a polyethylene glycol method, and a particle gun method. A method for regenerating a plant cell to a plant body may be determined depending on a type of the plant cell. For example, when a plant is papaya, a method by Fitch et al. (Fitch, M. M. M., Manshardt, R. M., Gonsalves, D., Slightom, J. L., Sanford, J. C., 1992, Biotechnology 10: 1466–1472) can be used to regenerate the plant cell to a plant body.

(4) Production of a Foreign Protein in a Plant

A method of the invention for producing a foreign protein in a plant comprises the following steps of 1) to 5).

1) cDNA is synthesized from genomic RNA of PLDMV. An example of the genomic RNA of PLDMV is an RNA comprising a nucleotide sequence as shown in SEQ ID NO: 1. Alternatively, an RNA comprising a nucleotide sequence as shown in SEQ ID NO: 1, having deletion, substitution, or addition of one or more nucleotides, and having infectious ability as a virus, may be used. cDNA can be synthesized by reverse transcription using a genomic RNA as a template.

Here, the full-length genomic RNA or a part of the genomic RNA may be used as a template.

2) A nucleotide sequence encoding an amino acid sequence which can be cleaved with a protease derived from PLDMV is added to the 5' terminus and the 3' terminus of a gene encoding a foreign protein to be produced. Thus, the resulting DNA fragment includes both the nucleotide sequence and the gene. The gene encoding the foreign protein is not specifically limited and may be any gene. Examples of the amino acid sequence which can be cleaved with a protease derived from PLDMV include Gln-Ala, Gln-Ser, Glu-Gly, and the like. These amino acid sequences can be cleaved with NIa-Protease (hereinafter referred to as "NIa-Pro") derived from PLDMV.

3) The DNA fragment of 2) is inserted into the cDNA of 1). The DNA fragment of 2) may be inserted into any position between P3 region and CP region of the cDNA of 1). The gene encoding the foreign protein can be inserted with, e.g., restriction enzymes.

4) RNA polymerase is allowed to act on the resulting cDNA of 3), and thereby synthesizing an RNA.

5) The RNA of 4) is allowed to infect a plant.

(5) A Protein Having a Protease Activity

The proteins of this invention are selected from the group consisting of the following (a) to (c):

(a) a protein comprising an amino acid sequence as shown in SEQ ID NO: 4;

(b) a protein comprising an amino acid sequence as shown in SEQ ID NO: 4 having deletion, substitution, or addition of one or more amino acids, and having a protease activity to cleave peptide bonds between Gln-Ala, Gln-Ser, and Glu-Gly; and (c) a protein derived from PLDMV encoded by a DNA which hybridizes to a DNA comprising a nucleotide sequence as shown in SEQ ID NO: 3 or a DNA complementary to said nucleotide sequence under stringent conditions, and having a protease activity to cleave peptide bonds between Gln-Ala, Gln-Ser, and Glu-Gly.

The protein of (a) is NIa-Pro (a fragment having a protease activity of NIa) which was obtained from PLDMV used in the following Example 1. The amino acid sequence of NIa-Pro is shown in SEQ ID NO: 4 and the nucleotide sequence coding for NIa-Pro is shown in SEQ ID NO: 3. The nucleotide sequence as shown in SEQ ID NO: 3 corresponds to the nucleotides 6772–7500 as shown in SEQ ID NO: 1.

The protein of (b) is a protein in which mutation is introduced without decreasing or losing a protease activity of the original protein. Examples of such mutation include, but are not limited to, naturally-occurring and artificial mutations. An example of a technique to cause an artificial mutation is, but is not limited to, site-specific mutagenesis (see, Nucleic Acids Res. 10, 6487–6500, 1982). The number of amino acids mutated is not limited, provided that it does not lose a protease activity of the protein to cleave peptide bonds between Gln-Ala, Gln-Ser and Glu-Gly. Generally, the number is within 30 amino acids, preferably within 20 amino acids, more preferably within 10 amino acids, and most preferably within 5 amino acids. The site of the protein responsible for the protease activity is G-x-C-G (Shukla, D. D., Ward, C. W. and Brunt, A. A. (1994) The potyviridae. CAB international, West Sussex.) which corresponds to the amino acids 149–152 (G-H-C-G) of NIa of PLDMV. Therefore, the mutation to the region except for the active site will not cause a lost of the protease activity, provide that the mutation will not change the conformation of the protein.

The protein of (c) is a protease derived from PLDMV which can be obtained by using a hybridization of DNAs. "Stringent conditions" used for the protein of (c) means conditions under which only specific hybridization occurs and non-specific hybridization does not occur. Such conditions are generally "1×SSC, 0.1% SDS, 37° C.", preferably "0.5×SSC, 0.1% SDS, 42° C.", more preferably "0.2×SSC, 0.1% SDS, 65° C.". A DNA obtained by such hybridization generally shows high homology with a DNA comprising a nucleotide sequence as shown in SEQ ID NO: 3. The term "high homology" used herein means 60% or more of homology, preferably 75% or more of homology, and more preferably 90% or more of homology.

The proteins of the invention (proteins of (a) to (c)) have a protease activity to cleave peptide bonds between Gln-Ala (between Q-A). Gln-Ser (between Q-S), and Glu-Gly (between E-G). This can be presumed from the following.

The polyproteins of Potyvirus include 10 types of proteins, such as P1, HC-Pro, P3, 6K1, CI, 6K2, NIa-VPg, NIa-Pro, NIb, and CP. Of these proteins, P1 and HC-Pro has self-cleavage activity, P3 and the other proteins can be cleaved with NIa-Pro. That is, NIa-Pro has a function to recognize and cleave peptide bonds between P3-6K1, 6K1-CI, CI-6K2, 6K2-NIa-VPg, NIa-VPg-NIa-Pro, NIa-Pro-NIb, and NIb-CP. Table 1 shows amino acid sequences at the N terminus and at the C terminus of each protein composing the polyprotein of Potyvirus. As shown in the table, for PLDMV, there are three types of combinations of N-terminus amino acid of one protein and C-terminus amino acid of another protein: Gln and Ala (Q and A), Gin and Ser (Q and S), as well as Glu and Gly (E and G). Therefore, NIa-Pro from PLDMV is thought to cleave the peptide bonds between Gln-Ala, Gln-Ser, and Glu-Gly.

Table 1 also shows amino acid sequences at the N terminus and the C terminus of each protein composing the polyprotein of Potyviruses other than PLDMV. The cleavage sites of NIa-Pro derived from each virus other than PLDMV, which are presumed from datas in this table, are thought to be quite different from those of NIa-Pro derived from PLDMV.

TABLE 1

Literature in which sequences are described and Accession numbers of Gen Bank

| Virus | P1/Hcpro/P3/6K1/CI/6K2/NIa-Vpg/NIa-pro/NIb/CP |
|---|---|
| PLDMV *1 | M—Y/S—G/G—Q/A—Q/S—Q/S—E/G—E/G—Q/S—Q/S—Y |
| PVY *1 | M—F/S—G/G—Q/R—Q/S—Q/A—Q/G—E/A—Q/A—Q/A—M |
| PepMoV *1 | M—Y/S—G/G—Q/R—Q/S—Q/S—Q/G—E/A—Q/A—Q/S—M |
| TVMV *1 | M—F/S—G/G—Q/A—Q/S—Q/S—Q/G—E/S—Q/G—Q/S—V |
| TEV *1 | M—Y/S—G/G—Q/A—Q/S—Q/S—Q/G—E/G—Q/G—Q/S—Q |
| SbMV *1 | M—Y/S—G/G—Q/A—Q/S—Q/S—Q/G—E/S—Q/G—Q/S—Q |

TABLE 1-continued

| Literature in which sequences are described and Accession numbers of Gen Bank | |
|---|---|
| Virus | P1/Hcpro/P3/6K1/CI/6K2/NIa-Vpg/NIa-pro/NIb/CP |
| PRSV *1 | M—Y/N—G/G—Q/A—Q/S—Q/S—Q/G—E/G—Q/S—Q/S—N |
| PSbMV *1 | M—F/S—G/G—Q/A—Q/S—Q/S—E/G—E/A—Q/S—Q/A—M |
| TuMV *1 | M—F/S—G/G—Q/A—Q/T—Q/S—E/A—E/S—Q/T—Q/A—L |
| JGMV *1 | M—Y/S—G/G—E/R—E/G—E/N—E/G—E/G—E/S—Q/S—I |
| PPV *1 | M—Y/S—G/G—Q/S—Q/S—Q/T—Q/G—E/S—Q/S—Q/A—V |
| JYMV-JI *2 | M—Y/S—G/G—Q/A—Q/A—Q/S—E/A—E/S—Q/M—Q/S—V |
| JYMV-M *3 | M—F/A—G/G—Q/A—Q/G—Q/S—E/A—E/S—Q/M—Q/S—V |
| SPFMV *4 | M—Y/S—G/G—Q/G—Q/S—Q/T—Q/G—E/S—Q/T—Q/S—V |
| RMV *5 | M—Y/S—G/G—Q/A—Q/S—Q/S—E/G—E/S—Q/S—E/A—L |
| PSV *6 | M—Y/S—G/G—Q/A—Q/S—Q/G—Q/G—E/S—Q/S—Q/S—Q |
| PVA *7 | M—L/S—S/A—Q/A—Q/A—Q/S—Q/S—E/S—Q/G—Q/A—V |

*1: Shukla, D. D., Ward, C. W. and Brunt, A. A. (1994). The potyviridae. CAB international, West Sussex.,
*2: AB016500,
*3: AB027007,
*4: NC 001841,
*5: NC 001814,
*6: NC 001723,
*7: NC 001649

BRIEF DESCRIPTION OF THE DRAWINGS

FIGS. 1*a* and 1*b* show the result of BLASTN homology search for P1 protein-coding region corresponds to a part of the sequence of the nucleotides 136–1575 as shown in SEQ ID NO: 1.

FIGS. 2*a* and 2*b* show the result of BLASTN homology search for a capsid protein (CP) coding region (nucleotides 9064–9945 as shown in SEQ ID NO: 1).

FIGS. 3*a* and 3*b* show the result of BLASTN homology search for a HC-Pro coding region (nucleotides 1576–2949).

FIGS. 4*a* and 4*b* show the result of BLASTN homology search for a NIb coding region (nucleotides 7501–9063).

PREFERRED EMBODIMENTS OF THE INVENTION

Figure 1B:
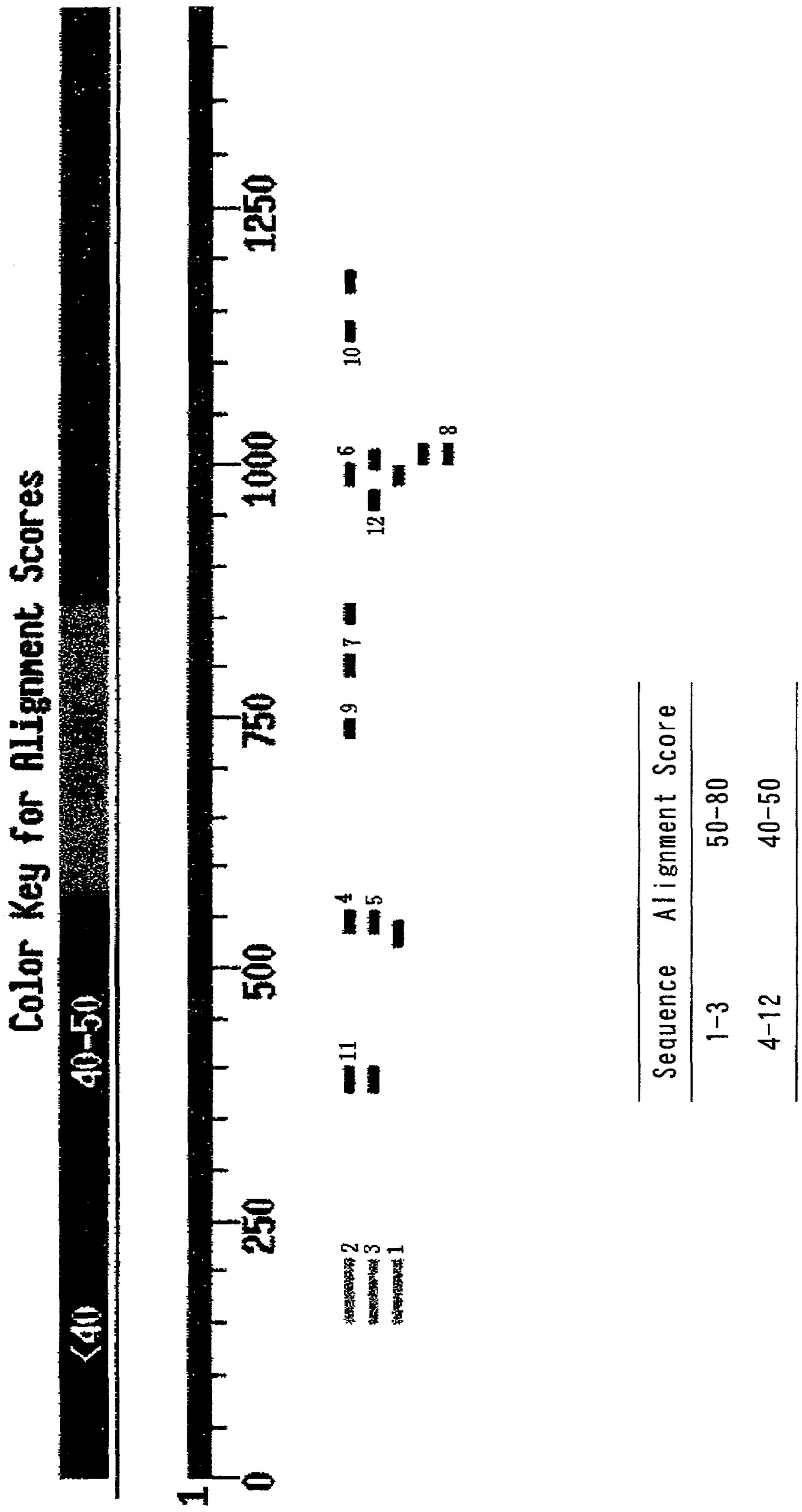
Figure 2B:
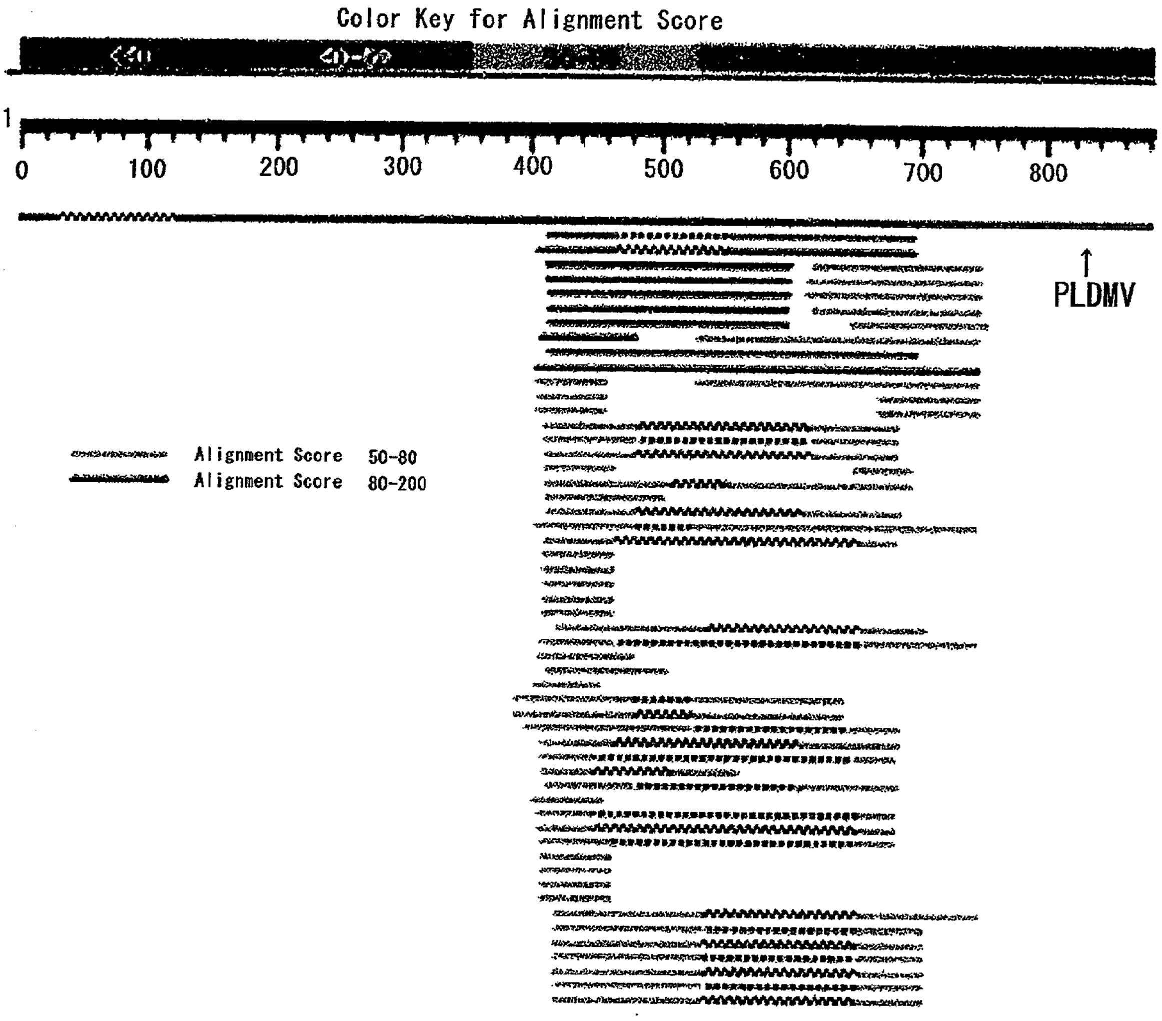
Figure 3B:
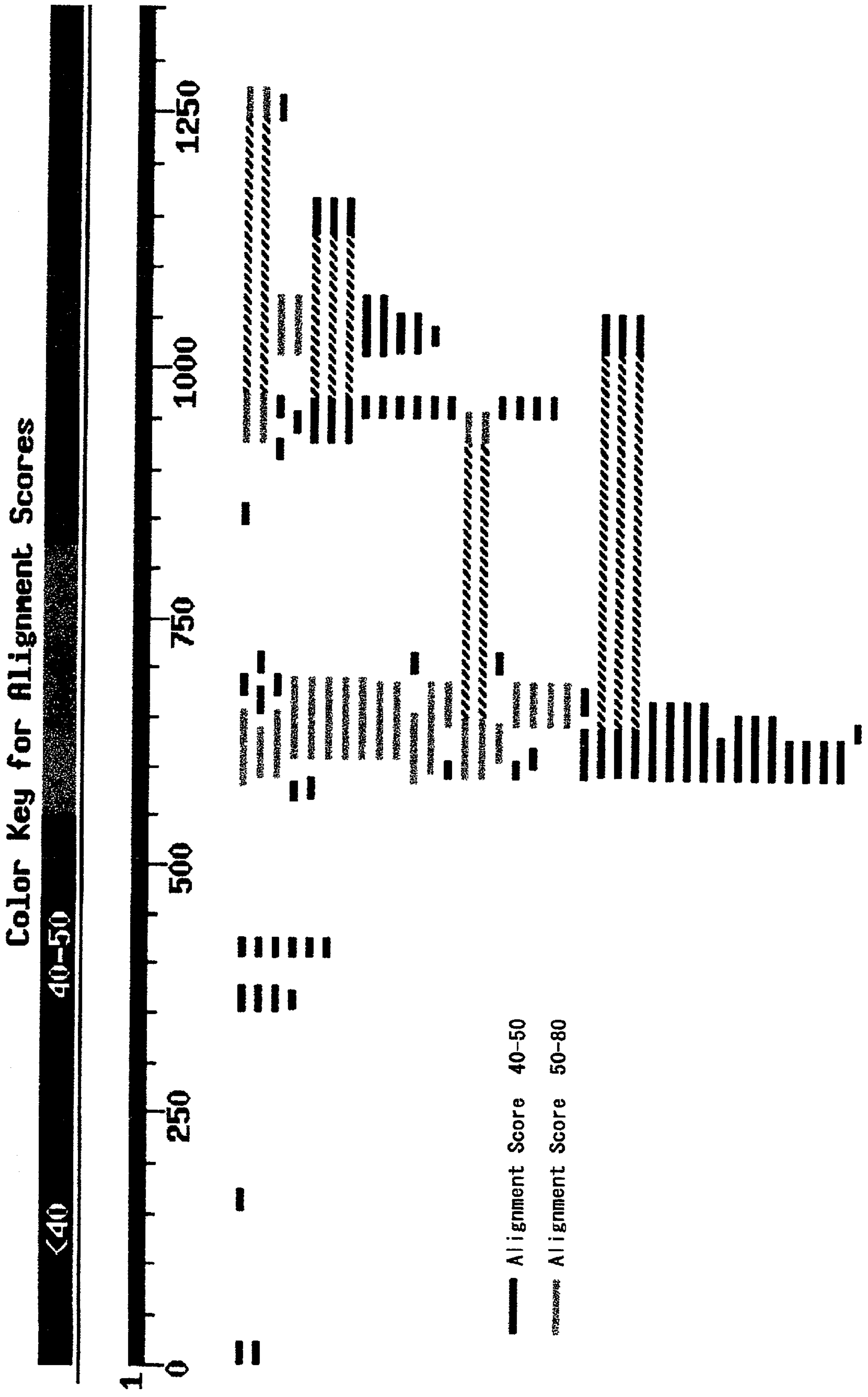
Figure 4B:
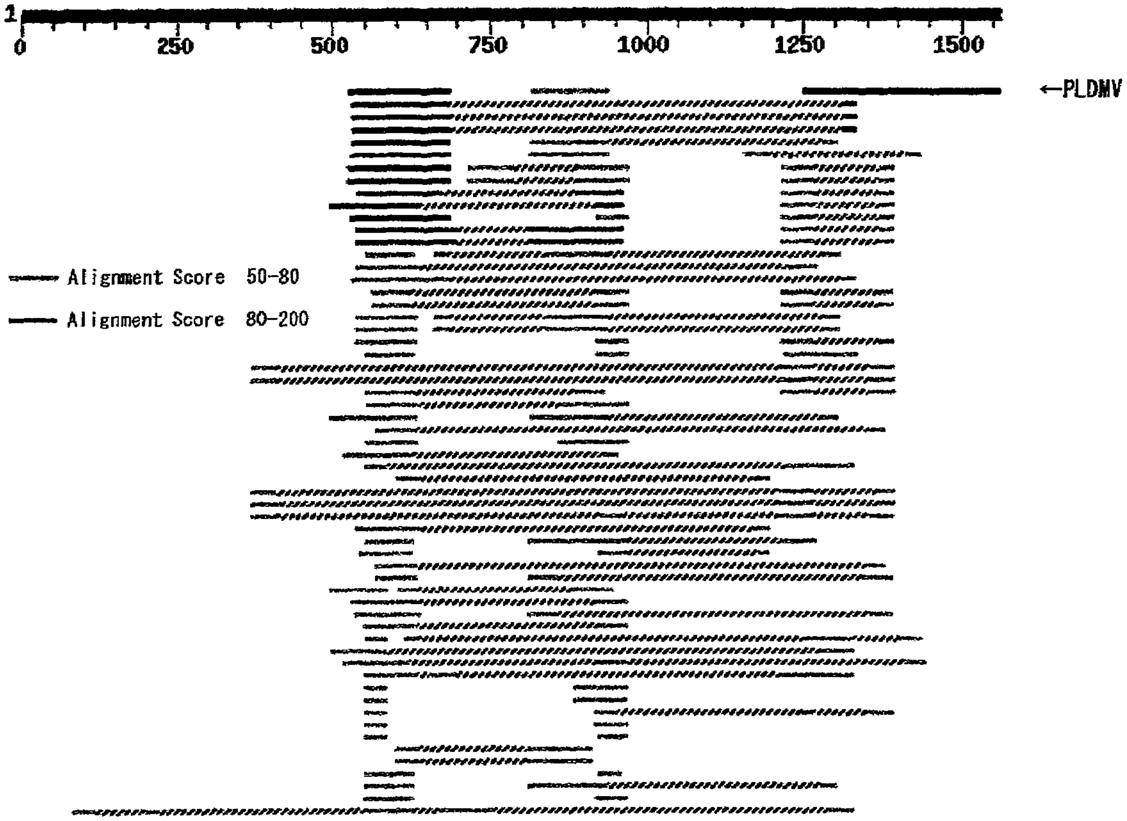

Hereinafter, the present invention will be described more specifically by use of the following examples. However, the technical scope of the invention is not limited to these examples.

EXAMPLE 1

Determination of the Nucleotide Sequence of PLDMV Periplastic Protein Gene (1) Isolation and Purification of a Virus 450 ml of 0.5M citrate buffer containing 0.56 g of sodium sulfite (this buffer had been prepared with 0. 5 M citric acid to pH 7. 0) was added to 140 g of *Cucumis metuliferus* inoculated with PLDMV, and then ground with a blender. The homogenate was squeezed through cotton cloth. Then, carbon tetrachloride was added to the filtrate, allowing the carbon tetrachloride to be 6% of the whole filtrate. After vigorous mixing, the filtrate was centrifuged at 6,000 g and 4° C. for 15 min, so that the supernatant was obtained. To 500 ml of the supernatant, 37.6 g of polyethylene glycol 6000, 2.92 g of sodium chloride, 10 ml of Triton ×100 were added. The mixture was stirred at 4° C. for 90 min, and then centrifuged at 6,000 g and 4° C. for 15 min. To the pellet precipitated after centrifugation, 0.1M citrate buffer containing 0.01M sodium sulfite (this buffer had been prepared with 0.1M citric acid to pH 7.0 and hereinafter referred to as a CD buffer) was added for re-suspension. The mixture was centrifuged at 6,000 g and 4° C. for 15 min, thereby obtaining the supernatant. Next, 30 ml of the supernatant was superposed over a 40% sucrose solution (prepared with CD buffer), and then centrifuged at 125,000 g for 90 min. Then the pellet was resuspended with 20 ml of a CD buffer, followed by centrifugation at 6,000 g and 4° C. for 15 min, thereby obtaining the supernatant. Subsequently, 10 ml of the supernatant was layered on 2 ml of a 40% sucrose solution (prepared with a CD buffer), followed by centrifugation at 125,000 g for 90 min. The pellet was resuspended with 2.5 ml of a CD buffer, centrifuged at 6,000 g and 4° C. for 15 min, thereby obtaining the supernatant. Then, the supernatant was layered on a linear density gradient of a cesium sulfate centrifugation (10–41%, Hitachi RPS40T rotor was used at 175,000 g and 6° C. for 15 hours) . Thus the obtained white band of a virus fraction was collected, diluted with a CD buffer, and then centrifuged at 238,000 g and 4° C. for 90 min. The precipitated virus pellet was resuspended with 0.3 ml of 0.01M citrate buffer (pH 7.0), thereby obtaining a purified sample of the virus.

(2) Preparation of PLDMV-RNA

RNA was extracted from the purified PLDMV above using a commercially available nucleic acid extraction kit, Sepagene (Sanko Junyaku Co., Ltd.). Extraction was performed according to the attached instructions.

(3) Construction and Screening of a cDNA Library

Since the viral RNA belonging to the genus Potyvirus has a poly A sequence at its 3' terminus, a double-stranded cDNA was synthesized using an oligo dT primer. A series of steps was taken with a commercially available cDNA synthesis kit (CLONTECH) according to the instructions attached to the kit. Adapter primers were linked to both ends of the synthesized cDNA. Next, PCR was performed using a downstream primer (NIb1) which is complementary to a known sequence of the NIb protein region of PLDMV, and using an upstream primer (AP1) of a sequence contained in the adapter primer. The amplified product was subjected to column purification, and then inserted to a cloning site of a phagemide vector pT7Blue (Novagen). Column purification was performed using SizeSep400 Spum Columns (Amersham Pharmacia Biotech) according to the attached instructions. The reaction product was transferred into *E. coli* strain JM109.

A small amount of plasmids were rapidly prepared from the PLDMV cDNA library obtained as described above, thereby obtaining a clone (NIb-99) having an approximately 2 Kb insert. The nucleotide sequence of the cDNA library was determined by the dideoxy method and analyzed with DNASIS (Hitachi Soft Engineering, Ver. 7.0).

Based on the upstream sequences of the determined nucleotide sequence, complementary primers were constructed. By repetition of the above described PCR, cloning, and sequencing, each clone (NIa-41, CI-64, 6K1-46, HC-23, and P1-40) was obtained from downstream to upstream. Further, PCR was performed using primers complementary to sequences upstream of CI-64, primers homologous to sequences upstream of HC-23, and using cDNA library as a template. Thus, a clone (P16K1-11) having an approximately 4 kb insert was obtained. The upstream sequence of PLDMV genome was determined from these clones.

(4) Determination of the 5' Terminal Sequence

Cloning of the 5' terminal portion of PLDMV gene has been tried several times by the 5' RACE method as described above. However, no plasmid containing this sequence was obtained. Then, primer extension was performed using the clone (P1-40) obtained in (3) above as a template, suggesting that 14 bases from the 5' terminus of PLDMV were not decoded yet. To elucidate the above sequence, improvement in the RNA purification method and the cloning method were tried.

TE (10 mM Tris-HCl pH 8.0, 1 mM EDTA) 68 μl, 10 μl of 20×SSC (3M NaCl, 0.3M sodium citrate pH 7.0), 2 μl of 20% SDS, and 20 μl of proteinase K (10 mg/ml) were added to 100 μl of the purified PLDMV, and the mixture was kept at 37° C. for 60 min. Next, 100 μl of 0.5% bentonite solution, and 200 μl of TE saturated phenol solution were added to the mixture. Then the mixture was shaken and centrifuged with an eppendolf small type centrifuge for 3 min, thereby obtaining the aqueous layer. After repeating the phenol extraction process as described above, 200 μl chloroform was added to the aqueous layer. The mixture was shaken, centrifuged with an eppendolf small type centrifuge for 3 min, thereby obtaining the aqueous layer. To the thus obtained aqueous layer, 25 μl of 3M sodium acetate solution (pH 5.2), and 500 μl of ethanol were added. The mixture was kept at −80° C. for 30 min, centrifuged with an eppendolf small type centrifuge for 10 min, thereby obtaining RNA as a precipitate. Next, 1 ml of 80% ethanol was added to the precipitate, followed by centrifugation with an eppendolf small type centrifuge for 3 min. Then, ethanol was removed, and RNA was dissolved in 100 μl of TE. In order to further increase purity of the RNA extract, the following steps were taken. 100 μl of 4M lithium chloride was added to the RNA solution, and then kept on ice for 4 hours, followed by centrifugation with an eppendolf small centrifuge for 10 min. 400 μl of 80% ethanol was added to the RNA precipitate, centrifuged for 3 min with an eppendolf small type centrifuge. After ethanol was removed, the RNA was dissolved in 12.5 μl of distilled water. Subsequently, 10 μl of 3M sodium acetate solution (pH 5.2) and 250 μl of ethanol were added to the mixture, kept at −80° C. for 30 min, and then centrifuged for 10 min with an eppendolf small type centrifuge, thereby obtaining RNA as the precipitate. One ml of 80% ethanol was added to the RNA, centrifuged for 3 min with an eppendolf small type centrifuge. After removal of ethanol, the RNA was dissolved in 10 μl of distilled water.

The cloning method was improved as follows. 1 μl of the complementary primer (P1–4) 100 pM solution that had been prepared based on the sequence of the upstream portion of the clone (HC-23), 2 μl of the purified PLDMV-RNA above, and 7 μl of distilled water were mixed and kept at 65° C. for 5 min. Next, 9.2 μl of distilled water, 9.0 μl of 4× RT buffer (CLONTECH), 1.6 μl of 40U/μl RNase Inhibitor (CLONTECH), 3.7 μl of dNTPmix (10 mM each), 0.5 μl of AMV Reverse Transcriptase (CLONTECH) were added to the solution, and then kept at 42° C. for 30 min. Thus ssDNA was synthesized. To this solution, 1 μl of 0.5M EDTA (pH 8.0) was added and mixed, and then placed on ice. Subsequently, 2 μl of 6N NaOH was added to the mixture, and kept at 65° C. for 30 min. After RNA was degraded, 2 μl of 6N acetic acid was added to and mixed with the mixture, followed by addition of 16 μl of distilled water. DNA was purified from the solution using a QIA quick PCR Purification Kit (QIAGEN). Purification was performed according to the attached instructions.

The above ssDNA 2.5 μl was added with 2 μl of anchor primer (Zhi, 1996), 5 μl of 2× Single-stranded Ligation Buffer (CLONTECH), 0.5 μl of 20 U/μl T4 RNA Ligase (CLONTECH), and 0.5 μl of 50 U/μl T4 RNA Ligase (TAKARA), and then allowed to stand at 22° C. overnight. Next, nested PCR was performed using this solution as a template, and a primer set (AP-B, P1–3) containing each sequence of the anchor primer and the complementary primer (P1–4) that had been used for reverse transcription reaction. Furthermore, nested PCR was performed using the reaction product as a template, and the more inward primer set (AP-C, P1–7). Then, cDNA was purified from the reaction product using a QIA quick PCR Purification Kit (QIAGEN), inserted into the cloning site of a phagemide vector pT7Blue (Novagen), thereby transferring into *E. coli* strain JM109. About 200 clones were selected from the cDNA library by colony PCR, thereby obtaining two clones (P1–7–6, P1–7–103) containing PLDMV 5' terminal sequences. Therefore, the 5' terminal sequence of PLDMV genome was decoded from these clones.

It was found that PLDMV genomic RNA comprised 10,155 bases, and had 6 bases of a poly A sequence at the 5' terminus followed by 129 bases of an untranslated region. There was an ORF starting from the initiation codon AUG at the 136th base from the 5' terminus and ending at the termination codon UAG at the 9943rd base. At the 3' terminus, there was another untranslated region comprising 210 bases following a termination codon, and a poly A sequence existed following A at the 10,155th base, as well. It was also found that PLDMV genomic RNA might comprise 5 bases of a poly A sequence and 129 bases of an untranslated region at the 5' terminus. Furthermore, the untranslated region at the 3' terminus may comprise 209 bases, and a poly A sequence may exist following G.

A polyprotein encoded by ORF consisted of 3269 amino acids. With reference to Shukla et al.'s report (Shukla, D. D., Ward, C. W. and Brunt, A. A., 1994, The potyviridae, CAB international, West Sussex), the positions of various protein genes of PLDMV were specified. Therefore, it was shown that P1 consists of 480 amino acids (nucleotides 136–1575 as shown in SEQ ID NO: 1), HC-Pro of 458 amino acids (nucleotides 1576–2949 as shown in SEQ ID NO: 1), P3 of 348 amino acids (nucleotides 2950–3993 as shown in SEQ ID NO: 1), 6K1 of 52 amino acids (nucleotides 3994–4149 as shown in SEQ ID NO: 1), CI of 635 amino acids (nucleotides 4150–6054 as shown in SEQ ID NO: 1), 6K2 of 52 amino acids (nucleotides 6055–6210 as shown in SEQ ID NO: 1), NIa-VPg of 187 amino acids (nucleotides 6211–6771 as shown in SEQ ID NO: 1), NIa-pro of 243 amino acids (nucleotides 6772–7500 as shown in SEQ ID NO: 1), NIb of 521 amino acids (nucleotides 7501–9063 as shown in SEQ ID NO: 1), and CP of 293 amino acids (nucleotides 9064–9945 as shown in SEQ ID NO: 1), all of which are shown in SEQ ID NOs: 1 and 2.

All publications, patents and patent applications cited herein are incorporated by reference in their entirety.

Elucidation of various protein gene structures of PLDMV of this invention enables detection of PLDMV gene by the RT-PCR method using the primers which are constructed based on the gene sequence. For example, there is a report that BYMV gene was detected from an infected plant by the RT-PCR method using primers that had been constructed based on the nucleotide sequence of bean yellow mosaic virus (BYMV) (Vunsh R, Rosner A, Stein A Ann Appl Biol 117: 561–569, 1990). Particularly, detection of P1 protein region with high species specificity allows highly accurate detection. For example, it has been reported that introduction of the periplastic protein gene of papaya ringspot virus type P (PRSV-P) into a papaya plant resulted in a virus-resistant plant (Tennant et al., Phytopathology 84; 1359–1366, 1994). That is, production of a PLDMV-resistant plant becomes possible by integrating the gene into the plant using genetic recombination techniques. Moreover, it has been reported that a foreign protein was produced in a plant body using an infectious clone of potato X virus or of tobacco mosaic virus as a vector (Ryabov, E. V. et al., Virology 242: 303–313, 1998). That is, insertion of a gene encoding a foreign protein into a PLDMV infectious clone allows use of the clone as an expression vector.

What is claimed is:

1. An isolated RNA comprising a nucleotide sequence as shown in SEQ ID NO: 1 or a nucleotide sequence complementary to said nucleotide sequence.

2. An isolated DNA comprising a nucleotide sequence as shown in SEQ ID NO: 1 in which uracil is replaced by thymine, or a nucleotide sequence complementary to said nucleotide sequence.

* * * * *

```
                              SEQUENCE LISTING


<160> NUMBER OF SEQ ID NOS: 4

<210> SEQ ID NO 1
<211> LENGTH: 10155
<212> TYPE: RNA
<213> ORGANISM: Papaya Leaf-Distortion Mosaic Virus
<220> FEATURE:
<221> NAME/KEY: CDS
<222> LOCATION: (136)..(9942)
<220> FEATURE:
<221> NAME/KEY: modified_base
<222> LOCATION: 1
<223> OTHER INFORMATION: n = a or deletion
<220> FEATURE:
<221> NAME/KEY: modified_base
<222> LOCATION: 10155
<223> OTHER INFORMATION: n = a or deletion

<400> SEQUENCE: 1

naaaaauaua aaaacucaac aaaacuuaug caaaacaauu ucaauacaca cacuuaacuu      60

ucauauugug caauucaaau cuuugcauua auucaacauu uccagcuuuu aaaacgaaua     120

acacacacag acaac aug ucg auu guu auu ggu gau uuu ucc auc cca cuc      171
                 Met Ser Ile Val Ile Gly Asp Phe Ser Ile Pro Leu
                 1               5                   10

auc ugc aga acu gag cag auu gaa ugu guu cgu cuu guu ccu gga aca       219
Ile Cys Arg Thr Glu Gln Ile Glu Cys Val Arg Leu Val Pro Gly Thr
        15                  20                  25

aga guu gaa gaa gug aag acc auu aaa aag guc uua aaa aca cac uac       267
Arg Val Glu Glu Val Lys Thr Ile Lys Lys Val Leu Lys Thr His Tyr
    30                  35                  40

caa gaa aua acu cuu ggu ugu acu gau aga ugc gcg ggc cug agc gca       315
Gln Glu Ile Thr Leu Gly Cys Thr Asp Arg Cys Ala Gly Leu Ser Ala
45                  50                  55                  60

uac aca aaa acc ucc cuu aag aga gca auu aag gaa aag gau uua acu       363
Tyr Thr Lys Thr Ser Leu Lys Arg Ala Ile Lys Glu Lys Asp Leu Thr
                65                  70                  75

gca ucu ggc agu ugu uuc cac ugu ggc cuu aga gca caa auc gga gag       411
Ala Ser Gly Ser Cys Phe His Cys Gly Leu Arg Ala Gln Ile Gly Glu
            80                  85                  90

ggu aga aaa agg gua gaa uua gca ccc auu uca guc aug gag gau guu       459
Gly Arg Lys Arg Val Glu Leu Ala Pro Ile Ser Val Met Glu Asp Val
        95                  100                 105

gaa acu gug gaa caa gua cuu guu cca ugu aug gua gaa gag aag uau       507
Glu Thr Val Glu Gln Val Leu Val Pro Cys Met Val Glu Glu Lys Tyr
    110                 115                 120
```

-continued

```
uau aag gaa guu ucg aau uuc cag aag gcu acg cuc auc gac aaa cca      555
Tyr Lys Glu Val Ser Asn Phe Gln Lys Ala Thr Leu Ile Asp Lys Pro
125                 130                 135                 140

aag cua acu aua gcc cca guu uua aug gca caa ccu gcc caa gug cca      603
Lys Leu Thr Ile Ala Pro Val Leu Met Ala Gln Pro Ala Gln Val Pro
                145                 150                 155

agg ccc gcu guu uuu aau gaa aua cga aaa guu cau gag gag aug aag      651
Arg Pro Ala Val Phe Asn Glu Ile Arg Lys Val His Glu Glu Met Lys
            160                 165                 170

ucc caa acc ucu gaa aac aag guc uua gaa gag gaa acu caa ugc gcc      699
Ser Gln Thr Ser Glu Asn Lys Val Leu Glu Glu Glu Thr Gln Cys Ala
        175                 180                 185

agu gau gca gcg cuu cac cac uua gac gac guu cau gcg ugu aga gcu      747
Ser Asp Ala Ala Leu His His Leu Asp Asp Val His Ala Cys Arg Ala
    190                 195                 200

cga gca cag gua ggc auu gaa cgc aua cua gcc aga cau gca agg cau      795
Arg Ala Gln Val Gly Ile Glu Arg Ile Leu Ala Arg His Ala Arg His
205                 210                 215                 220

aga auc gag gcu aga cag caa guu gaa gag gag caa ucg gaa gca uua      843
Arg Ile Glu Ala Arg Gln Gln Val Glu Glu Glu Gln Ser Glu Ala Leu
                225                 230                 235

gca gcg uuc gaa ucc uuc uuc aau caa acu cac aga gaa gac aga uau      891
Ala Ala Phe Glu Ser Phe Phe Asn Gln Thr His Arg Glu Asp Arg Tyr
            240                 245                 250

gaa ggg aaa guc uua acc auu cga aau ggg auc aca ggc ugg uuu gaa      939
Glu Gly Lys Val Leu Thr Ile Arg Asn Gly Ile Thr Gly Trp Phe Glu
        255                 260                 265

cca aau agg aau gau auu aag aac gca gcu agg cgg agg aag aga gcu      987
Pro Asn Arg Asn Asp Ile Lys Asn Ala Ala Arg Arg Arg Lys Arg Ala
    270                 275                 280

aac aag aaa auc ccg uuu guu gca cgu gaa aau gac guc gcg cgg aua     1035
Asn Lys Lys Ile Pro Phe Val Ala Arg Glu Asn Asp Val Ala Arg Ile
285                 290                 295                 300

gaa acu cau gaa ccu aac guc aaa gag gag aca aaa gau gug gag gaa     1083
Glu Thr His Glu Pro Asn Val Lys Glu Glu Thr Lys Asp Val Glu Glu
                305                 310                 315

gca acu gac aca uac aca uuu aag aag cag cgc aau gau aaa aag aga     1131
Ala Thr Asp Thr Tyr Thr Phe Lys Lys Gln Arg Asn Asp Lys Lys Arg
            320                 325                 330

gug cug aaa gaa aau gug ucu cuu agu aug gcg cgc auu aau gaa cuu     1179
Val Leu Lys Glu Asn Val Ser Leu Ser Met Ala Arg Ile Asn Glu Leu
        335                 340                 345

guc cga ugu guu aca aaa uua ugc cga aaa gau uca aag gag cuu gag     1227
Val Arg Cys Val Thr Lys Leu Cys Arg Lys Asp Ser Lys Glu Leu Glu
    350                 355                 360

uuu auc ggc aag aga gga agu cuu cga guu caa ugu acu aaa aau ugu     1275
Phe Ile Gly Lys Arg Gly Ser Leu Arg Val Gln Cys Thr Lys Asn Cys
365                 370                 375                 380

ggu uca cga gug aua cua aga cac uug cgu gga gaa cuu aga aga aaa     1323
Gly Ser Arg Val Ile Leu Arg His Leu Arg Gly Glu Leu Arg Arg Lys
                385                 390                 395

gau ugu uau ugg gau cgu auc auu gag aau uuc uuu gaa auu gca gcu     1371
Asp Cys Tyr Trp Asp Arg Ile Ile Glu Asn Phe Phe Glu Ile Ala Ala
            400                 405                 410

gca aag cuu cag aau aag aau cuc aau aac aau gaa ucu gug agg aga     1419
Ala Lys Leu Gln Asn Lys Asn Leu Asn Asn Asn Glu Ser Val Arg Arg
        415                 420                 425

ggg cac agu gga cau auc auu caa uau gau aag uuu aga ggu uug agu     1467
Gly His Ser Gly His Ile Ile Gln Tyr Asp Lys Phe Arg Gly Leu Ser
```

-continued

```
    430                 435                 440

gga cgg cau uuc gga agu uac auc auu guu agg ggu agc aug gau ggc      1515
Gly Arg His Phe Gly Ser Tyr Ile Ile Val Arg Gly Ser Met Asp Gly
445                 450                 455                 460

aga auu auu gac gcu cgu uca aag auc aca cac agc guu aug auc aac      1563
Arg Ile Ile Asp Ala Arg Ser Lys Ile Thr His Ser Val Met Ile Asn
                465                 470                 475

aug acc cac uac agu gau gca ggu uug agu uuu ugg aaa ggu uuu gau      1611
Met Thr His Tyr Ser Asp Ala Gly Leu Ser Phe Trp Lys Gly Phe Asp
            480                 485                 490

cgu caa uuu auu gac auu cga gau aga ccu aag aac gcu cau gag ugc      1659
Arg Gln Phe Ile Asp Ile Arg Asp Arg Pro Lys Asn Ala His Glu Cys
        495                 500                 505

aag gcc acu aua aac guu gag gag ugu ggc gaa aug gca gcc auu gua      1707
Lys Ala Thr Ile Asn Val Glu Glu Cys Gly Glu Met Ala Ala Ile Val
    510                 515                 520

aac caa cuc cua uuu cca aug ugg aaa aua aca ugc acu caa ugu gga      1755
Asn Gln Leu Leu Phe Pro Met Trp Lys Ile Thr Cys Thr Gln Cys Gly
525                 530                 535                 540

gaa cug cuu gaa aug uug uca caa gaa gag gaa cuu gaa ucu uuc agg      1803
Glu Leu Leu Glu Met Leu Ser Gln Glu Glu Glu Leu Glu Ser Phe Arg
                545                 550                 555

cgu aaa agg agc caa uug gca agu aaa uua ucc agu cuu cau auc aaa      1851
Arg Lys Arg Ser Gln Leu Ala Ser Lys Leu Ser Ser Leu His Ile Lys
            560                 565                 570

uuu ccu uac gug gau cau uuu cuu aau cga uau gag aau agu cug aau      1899
Phe Pro Tyr Val Asp His Phe Leu Asn Arg Tyr Glu Asn Ser Leu Asn
        575                 580                 585

cgg aug aac aca aac uuc gau gcg cac aaa caa auu gca caa auu auu      1947
Arg Met Asn Thr Asn Phe Asp Ala His Lys Gln Ile Ala Gln Ile Ile
    590                 595                 600

ggc agu cgc aaa gag auu ccu uuu uca aau uua gag cau cug aau gaa      1995
Gly Ser Arg Lys Glu Ile Pro Phe Ser Asn Leu Glu His Leu Asn Glu
605                 610                 615                 620

uug cua auu aag ucg gau aaa cuu guu agc gag gau uuc uau gaa aug      2043
Leu Leu Ile Lys Ser Asp Lys Leu Val Ser Glu Asp Phe Tyr Glu Met
                625                 630                 635

ucu caa ugc cuu uua gag cua aca cgc ugg cau aaa aac agg agc gau      2091
Ser Gln Cys Leu Leu Glu Leu Thr Arg Trp His Lys Asn Arg Ser Asp
            640                 645                 650

uca uuc aag aag gga gag auu cac cau uuc cga aau aag aug uca ggu      2139
Ser Phe Lys Lys Gly Glu Ile His His Phe Arg Asn Lys Met Ser Gly
        655                 660                 665

aaa gca caa uuu aau uuu gca uug aug ugu gac aac caa cuu gac aaa      2187
Lys Ala Gln Phe Asn Phe Ala Leu Met Cys Asp Asn Gln Leu Asp Lys
    670                 675                 680

aau ggu aac uuc gug ugg ggu gaa aga ggu uau cau gcg aag agg uuu      2235
Asn Gly Asn Phe Val Trp Gly Glu Arg Gly Tyr His Ala Lys Arg Phe
685                 690                 695                 700

uuc uua aac uuc uuu gag aaa guu gau uca acu gac ggu uau aag aaa      2283
Phe Leu Asn Phe Phe Glu Lys Val Asp Ser Thr Asp Gly Tyr Lys Lys
                705                 710                 715

cac aua aug cga guc aac cca aau ggc aca aga caa aca gcu aua gga      2331
His Ile Met Arg Val Asn Pro Asn Gly Thr Arg Gln Thr Ala Ile Gly
            720                 725                 730

aaa cug auu uua ucg acg gau cca ucu acg cua cga caa caa aug aaa      2379
Lys Leu Ile Leu Ser Thr Asp Pro Ser Thr Leu Arg Gln Gln Met Lys
        735                 740                 745

ggu agc cca auc aca aga guu cca guu ggu aaa uau ugu aca agc aaa      2427
```

-continued

```
Gly Ser Pro Ile Thr Arg Val Pro Val Gly Lys Tyr Cys Thr Ser Lys
    750                 755                 760

aga gau ggu ugu uac guc uau cca gca ugc ugu guu aca aug gaa gau      2475
Arg Asp Gly Cys Tyr Val Tyr Pro Ala Cys Cys Val Thr Met Glu Asp
765                 770                 775                 780

ggu acg cca uug uuu ucu gau auc aag aug cca acu aag aau cau cua      2523
Gly Thr Pro Leu Phe Ser Asp Ile Lys Met Pro Thr Lys Asn His Leu
                785                 790                 795

guc auu gga aau uca gga gau cca aag uau gug gau gua cca agc agc      2571
Val Ile Gly Asn Ser Gly Asp Pro Lys Tyr Val Asp Val Pro Ser Ser
            800                 805                 810

uca agu gac aug auu gug gcu aag gaa ggu uau ugu uau cuc aac auu      2619
Ser Ser Asp Met Ile Val Ala Lys Glu Gly Tyr Cys Tyr Leu Asn Ile
        815                 820                 825

uuc uug gca aug uug cug aau gug aau gag agu gaa uca aaa uca uuc      2667
Phe Leu Ala Met Leu Leu Asn Val Asn Glu Ser Glu Ser Lys Ser Phe
    830                 835                 840

aca aag aag guu aga gau aua auu gua ccg cgu cuc ggu caa ugg cca      2715
Thr Lys Lys Val Arg Asp Ile Ile Val Pro Arg Leu Gly Gln Trp Pro
845                 850                 855                 860

agc uua auc gau guu gca acu gaa ugu uac uuc cua uca gcc uuc cac      2763
Ser Leu Ile Asp Val Ala Thr Glu Cys Tyr Phe Leu Ser Ala Phe His
                865                 870                 875

ccu gaa acg aaa aau gcu gag uug ccc cga auu cua gug gau cau aca      2811
Pro Glu Thr Lys Asn Ala Glu Leu Pro Arg Ile Leu Val Asp His Thr
            880                 885                 890

uca aaa ugu aug cau gug auc gau uca uau ggc ucg cua gac acg caa      2859
Ser Lys Cys Met His Val Ile Asp Ser Tyr Gly Ser Leu Asp Thr Gln
        895                 900                 905

uuu cau guu cug aag gca aau acu gua agu cag cua auu aaa uuc gcc      2907
Phe His Val Leu Lys Ala Asn Thr Val Ser Gln Leu Ile Lys Phe Ala
    910                 915                 920

gau aau gac uug gau ucg gag cug aaa cau uau uua gua ggu gga gac      2955
Asp Asn Asp Leu Asp Ser Glu Leu Lys His Tyr Leu Val Gly Gly Asp
925                 930                 935                 940

cuc cau agc aag caa gcu ccu cag ugu ucc aua aaa uua cuc ugu aaa      3003
Leu His Ser Lys Gln Ala Pro Gln Cys Ser Ile Lys Leu Leu Cys Lys
                945                 950                 955

ugu aua uau agg ccu aaa uug aug agg caa ugc auu gag gaa gag ccu      3051
Cys Ile Tyr Arg Pro Lys Leu Met Arg Gln Cys Ile Glu Glu Glu Pro
            960                 965                 970

uuu uug uug auu uua gcg ugu auc uca cca ggu guu uua uua gcu uua      3099
Phe Leu Leu Ile Leu Ala Cys Ile Ser Pro Gly Val Leu Leu Ala Leu
        975                 980                 985

uau aau agu cag cau uua gaa uua gcu uua aag uac ugg aug agc aag      3147
Tyr Asn Ser Gln His Leu Glu Leu Ala Leu Lys Tyr Trp Met Ser Lys
    990                 995                 1000

caa cag ucu guc gcu gcu uua uuu gca aug auc cau gga cua gcu gca      3195
Gln Gln Ser Val Ala Ala Leu Phe Ala Met Ile His Gly Leu Ala Ala
1005                1010                1015                1020

aaa gua aca guu gcu caa aca uug aau gag cag aga cua aua cuu gaa      3243
Lys Val Thr Val Ala Gln Thr Leu Asn Glu Gln Arg Leu Ile Leu Glu
                1025                1030                1035

cgc ggg gcg cgc aau uug auu ucg guc aug gaa acc aua cac aug aca      3291
Arg Gly Ala Arg Asn Leu Ile Ser Val Met Glu Thr Ile His Met Thr
            1040                1045                1050

agc cau uca uac caa ccc  gcg cuu cuu caa cua cag guc aug gca aau     3339
Ser His Ser Tyr Gln Pro Ala Leu Leu Gln Leu Gln Val Met Ala Asn
        1055                1060                1065
```

-continued

```
cgu aga gac aug aau ucc acu cuu gau cuc gcc gga uuc agc aua uua      3387
Arg Arg Asp Met Asn Ser Thr Leu Asp Leu Ala Gly Phe Ser Ile Leu
    1070                1075                1080

caa ucu gaa gau agu aug uau ugg aug gaa aaa agu uau cuc aug gaa      3435
Gln Ser Glu Asp Ser Met Tyr Trp Met Glu Lys Ser Tyr Leu Met Glu
1085                1090                1095                1100

uua gag gau ucg ugg aac gac uua aag ugg uug gaa aaa uua caa gaa      3483
Leu Glu Asp Ser Trp Asn Asp Leu Lys Trp Leu Glu Lys Leu Gln Glu
                1105                1110                1115

aug ugg cga uua uca aag uac uca aua ucu ggg aua agu caa cuu uca      3531
Met Trp Arg Leu Ser Lys Tyr Ser Ile Ser Gly Ile Ser Gln Leu Ser
            1120                1125                1130

aug aaa ggc gcu acc gau uua ggc ggu cga uau uca gua ucu gca aag      3579
Met Lys Gly Ala Thr Asp Leu Gly Gly Arg Tyr Ser Val Ser Ala Lys
        1135                1140                1145

cag uuu aua aca uca gug aug aaa ccu guc aag aaa ucu ugu gua aaa      3627
Gln Phe Ile Thr Ser Val Met Lys Pro Val Lys Lys Ser Cys Val Lys
    1150                1155                1160

gca aga gau acu ugu aag gaa gua auc auc aau aca aca ucc ugg aca      3675
Ala Arg Asp Thr Cys Lys Glu Val Ile Ile Asn Thr Thr Ser Trp Thr
1165                1170                1175                1180

uuu cgg gca aca uuu ucu uug ugu agg ugg ugc uug ccu gau ugu uug      3723
Phe Arg Ala Thr Phe Ser Leu Cys Arg Trp Cys Leu Pro Asp Cys Leu
                1185                1190                1195

aag uuu aua aac aug cuu aua guu aua agu uug auu cuc agc auu ugg      3771
Lys Phe Ile Asn Met Leu Ile Val Ile Ser Leu Ile Leu Ser Ile Trp
            1200                1205                1210

cau uca gcu aau ucu aua ucg uuc gac uau gca caa aug aag aga gaa      3819
His Ser Ala Asn Ser Ile Ser Phe Asp Tyr Ala Gln Met Lys Arg Glu
        1215                1220                1225

aag cag gug aau auc gag aaa guu cug aug aau aau uua gug gcc cuu      3867
Lys Gln Val Asn Ile Glu Lys Val Leu Met Asn Asn Leu Val Ala Leu
    1230                1235                1240

cau aag gag cag aua aag auc aau cca gac cug aca aag gaa gaa uuu      3915
His Lys Glu Gln Ile Lys Ile Asn Pro Asp Leu Thr Lys Glu Glu Phe
1245                1250                1255                1260

aag gag uac auu gca aga agu aga ccu gag cug auu gca uua guu aau      3963
Lys Glu Tyr Ile Ala Arg Ser Arg Pro Glu Leu Ile Ala Leu Val Asn
                1265                1270                1275

aaa gaa uug caa gaa gaa guu gau cau caa gcu aag cgc aaa ggu gaa      4011
Lys Glu Leu Gln Glu Glu Val Asp His Gln Ala Lys Arg Lys Gly Glu
            1280                1285                1290

caa aac uug gag aaa auu aua gca uuu guu gcc uua guu aug aug auu      4059
Gln Asn Leu Glu Lys Ile Ile Ala Phe Val Ala Leu Val Met Met Ile
        1295                1300                1305

uuu gac uca gag aaa agu gau ugu gua uau aag aca cug aac aaa uug      4107
Phe Asp Ser Glu Lys Ser Asp Cys Val Tyr Lys Thr Leu Asn Lys Leu
    1310                1315                1320

cga aau cuc guu gcc aca ugu gau gaa ccu guc gca cau caa agc uug      4155
Arg Asn Leu Val Ala Thr Cys Asp Glu Pro Val Ala His Gln Ser Leu
1325                1330                1335                1340

gac gac auu caa gac auc uug acu gac aaa gaa aca acc auu gau uuc      4203
Asp Asp Ile Gln Asp Ile Leu Thr Asp Lys Glu Thr Thr Ile Asp Phe
                1345                1350                1355

gac uua gau ugu gag ggg agc aaa guu aca gag uuc aag gag aug aac      4251
Asp Leu Asp Cys Glu Gly Ser Lys Val Thr Glu Phe Lys Glu Met Asn
            1360                1365                1370

uuu gcc gca ugg ugg gaa aaa caa cua caa ugu gau aga gug gua ccc      4299
Phe Ala Ala Trp Trp Glu Lys Gln Leu Gln Cys Asp Arg Val Val Pro
        1375                1380                1385
```

-continued

```
cau uau aga acc acu ggg aaa uuu auu gaa uuc acu cgu gaa agc ugu      4347
His Tyr Arg Thr Thr Gly Lys Phe Ile Glu Phe Thr Arg Glu Ser Cys
    1390                1395                1400

guu agu gug agu aac aca aua ucu cau gcc ccu gag aaa gaa ugg aua      4395
Val Ser Val Ser Asn Thr Ile Ser His Ala Pro Glu Lys Glu Trp Ile
1405                1410                1415                1420

guc cgu ggu ggu guu gga uca gga aaa ucu acu ggu cua cca uuc gcg      4443
Val Arg Gly Gly Val Gly Ser Gly Lys Ser Thr Gly Leu Pro Phe Ala
                1425                1430                1435

uua ucu agu aaa ggc gca guu cuu aug cuc gaa cca aca aga cca uug      4491
Leu Ser Ser Lys Gly Ala Val Leu Met Leu Glu Pro Thr Arg Pro Leu
            1440                1445                1450

gca gag aau guc uca cga cag uug aga caa cau ccc uuu uau gca aac      4539
Ala Glu Asn Val Ser Arg Gln Leu Arg Gln His Pro Phe Tyr Ala Asn
        1455                1460                1465

ccc aca uug aga aug cga gga aug uca ucu uuu gga ucu agu aau aua      4587
Pro Thr Leu Arg Met Arg Gly Met Ser Ser Phe Gly Ser Ser Asn Ile
    1470                1475                1480

ugu aua aug acu agu gga uuu gcu uuc aau uac uuu gca aau aau ccu      4635
Cys Ile Met Thr Ser Gly Phe Ala Phe Asn Tyr Phe Ala Asn Asn Pro
1485                1490                1495                1500

cua aaa uua agu gau uuu gaa uuu gug aua aua gau gag ugu cac guc      4683
Leu Lys Leu Ser Asp Phe Glu Phe Val Ile Ile Asp Glu Cys His Val
                1505                1510                1515

cua gau agc aac gcu aug gca uuc gug ugu cuu cuc aaa gaa cac aac      4731
Leu Asp Ser Asn Ala Met Ala Phe Val Cys Leu Leu Lys Glu His Asn
            1520                1525                1530

uau gau ggc aaa cua uug aaa gug uca gcc aca cca cag ggc cgu gaa      4779
Tyr Asp Gly Lys Leu Leu Lys Val Ser Ala Thr Pro Gln Gly Arg Glu
        1535                1540                1545

ugu gaa uuc cac aca cag cau cca guu ucc auu cau aua gag gaa caa      4827
Cys Glu Phe His Thr Gln His Pro Val Ser Ile His Ile Glu Glu Gln
    1550                1555                1560

cuu agu uuc caa gcu uuu ugu gaa gcu caa gga acu ggg ucu gca cga      4875
Leu Ser Phe Gln Ala Phe Cys Glu Ala Gln Gly Thr Gly Ser Ala Arg
1565                1570                1575                1580

gau gua auc aau aag gga gac aac auu uua gug uau guu gcu agu uac      4923
Asp Val Ile Asn Lys Gly Asp Asn Ile Leu Val Tyr Val Ala Ser Tyr
                1585                1590                1595

aau gag guu gau cag cuc uca aaa aug cuc gga gau aaa ggc uau uua      4971
Asn Glu Val Asp Gln Leu Ser Lys Met Leu Gly Asp Lys Gly Tyr Leu
            1600                1605                1610

gug acu aaa guc gau ggg cgu acc aug aaa auu ggu ucg acc gac aua      5019
Val Thr Lys Val Asp Gly Arg Thr Met Lys Ile Gly Ser Thr Asp Ile
        1615                1620                1625

guu acu aaa ggg agu agc cag aag aaa cau uuc auu gua gca acc aac      5067
Val Thr Lys Gly Ser Ser Gln Lys Lys His Phe Ile Val Ala Thr Asn
    1630                1635                1640

aua auc gag aau gga guc acu cua gau gua gau guu guu gug gac uuu      5115
Ile Ile Glu Asn Gly Val Thr Leu Asp Val Asp Val Val Val Asp Phe
1645                1650                1655                1660

ggu uug aaa guc acu gcu gaa auu gau uac gac aac cgg ugc guu aau      5163
Gly Leu Lys Val Thr Ala Glu Ile Asp Tyr Asp Asn Arg Cys Val Asn
                1665                1670                1675

uac aca aag acc agc auu uca uac gga gaa cgc aua caa aga uug ggc      5211
Tyr Thr Lys Thr Ser Ile Ser Tyr Gly Glu Arg Ile Gln Arg Leu Gly
            1680                1685                1690

agg guu ggu aga cac aag aaa ggg cau gca aug aga auu gga acu aca      5259
Arg Val Gly Arg His Lys Lys Gly His Ala Met Arg Ile Gly Thr Thr
```

-continued

```
        1695                1700                1705

auu aaa gga uug auu gag auu ccu agu cuu gug gcg aca cag gcu gca      5307
Ile Lys Gly Leu Ile Glu Ile Pro Ser Leu Val Ala Thr Gln Ala Ala
    1710                1715                1720

uuu caa ugc uuc aca uau gga uug ccu gua aug aca caa gga guu uca      5355
Phe Gln Cys Phe Thr Tyr Gly Leu Pro Val Met Thr Gln Gly Val Ser
1725                1730                1735                1740

guu aac agu uua uca aau ugc aca guc cga cag gcc aga guu aug ucu      5403
Val Asn Ser Leu Ser Asn Cys Thr Val Arg Gln Ala Arg Val Met Ser
                1745                1750                1755

cgu uuu gag uug ccg ccu uac uuu aug gcu uca cuu gua uau cau gau      5451
Arg Phe Glu Leu Pro Pro Tyr Phe Met Ala Ser Leu Val Tyr His Asp
            1760                1765                1770

ggc agc aug cac ccu gaa auu cac aag cau uua auu ccu uac aag uua      5499
Gly Ser Met His Pro Glu Ile His Lys His Leu Ile Pro Tyr Lys Leu
        1775                1780                1785

gau gaa ucu gaa auu caa cuu agu gcc aug gcu uuu aac uuu acc gua      5547
Asp Glu Ser Glu Ile Gln Leu Ser Ala Met Ala Phe Asn Phe Thr Val
    1790                1795                1800

aca ucu auu ugg cua gau ugu aaa uuu uau gac agu aua gga auc cau      5595
Thr Ser Ile Trp Leu Asp Cys Lys Phe Tyr Asp Ser Ile Gly Ile His
1805                1810                1815                1820

cuu gau uua ccg cgc gaa gca aaa auu cca uuc cau ugu aga gaa uuc      5643
Leu Asp Leu Pro Arg Glu Ala Lys Ile Pro Phe His Cys Arg Glu Phe
                1825                1830                1835

cca gau aug aaa uac cga cac uug ugg gaa gau auu cuc aaa auc aag      5691
Pro Asp Met Lys Tyr Arg His Leu Trp Glu Asp Ile Leu Lys Ile Lys
            1840                1845                1850

agc aua aau ugu uuu ggu aga aug agu guu guu agc gca aca aaa gua      5739
Ser Ile Asn Cys Phe Gly Arg Met Ser Val Val Ser Ala Thr Lys Val
        1855                1860                1865

gca uau aca cuu aaa aca gac auu cau uca auu gga aaa acu cuc gga      5787
Ala Tyr Thr Leu Lys Thr Asp Ile His Ser Ile Gly Lys Thr Leu Gly
    1870                1875                1880

uau auu gac gcc cuc uug caa gaa gaa uau aga aaa cag cau cau uuu      5835
Tyr Ile Asp Ala Leu Leu Gln Glu Glu Tyr Arg Lys Gln His His Phe
1885                1890                1895                1900

aaa gca aug aca agu aac gca ugu agu ggg aac acu uuu uca aug cua      5883
Lys Ala Met Thr Ser Asn Ala Cys Ser Gly Asn Thr Phe Ser Met Leu
                1905                1910                1915

agc aua gca aau gca aua cgg aac cac uau gcu aag gac uac acu gcu      5931
Ser Ile Ala Asn Ala Ile Arg Asn His Tyr Ala Lys Asp Tyr Thr Ala
            1920                1925                1930

ggc aau auu cag aaa uug cag gca gca aag aau caa aua cug gaa uuc      5979
Gly Asn Ile Gln Lys Leu Gln Ala Ala Lys Asn Gln Ile Leu Glu Phe
        1935                1940                1945

guc aau uua aau cuu gau ccu ucg gcg aaa ugc gga uuc caa gag uuc      6027
Val Asn Leu Asn Leu Asp Pro Ser Ala Lys Cys Gly Phe Gln Glu Phe
    1950                1955                1960

gga gcu uua gaa cua guu acc cau cag agc agg caa gaa auu uca aaa      6075
Gly Ala Leu Glu Leu Val Thr His Gln Ser Arg Gln Glu Ile Ser Lys
1965                1970                1975                1980

uuu cua aau cug aga ggu aag ugg aau aag uca cua auu aca cgu gau      6123
Phe Leu Asn Leu Arg Gly Lys Trp Asn Lys Ser Leu Ile Thr Arg Asp
                1985                1990                1995

auc uua guu uug uua ggu guc acu auu ggu ggu uuc ugg aug aua ugg      6171
Ile Leu Val Leu Leu Gly Val Thr Ile Gly Gly Phe Trp Met Ile Trp
            2000                2005                2010

gau aag uuc aaa uca aac auu gaa gaa guu cau cau gaa gga aag agg      6219
```

-continued

```
Asp Lys Phe Lys Ser Asn Ile Glu Glu Val His His Glu Gly Lys Arg
        2015                2020                2025

aag acu caa aag cuu aaa uuu cgg gau gcu cgc gau aag aaa aug ggu      6267
Lys Thr Gln Lys Leu Lys Phe Arg Asp Ala Arg Asp Lys Lys Met Gly
    2030                2035                2040

cga gaa gua uau gga gac gac ggu acu auu gaa cau uac uuu gga ucg      6315
Arg Glu Val Tyr Gly Asp Asp Gly Thr Ile Glu His Tyr Phe Gly Ser
2045                2050                2055                2060

gca uac guc aag aga ggu gca guu aag ggc cag aag aga gga aug ggc      6363
Ala Tyr Val Lys Arg Gly Ala Val Lys Gly Gln Lys Arg Gly Met Gly
                2065                2070                2075

gaa aaa uca aga cgu uuc guu agu aug uau gga guu aau uua gaa gau      6411
Glu Lys Ser Arg Arg Phe Val Ser Met Tyr Gly Val Asn Leu Glu Asp
            2080                2085                2090

uuu gcu uuu auu aga uac aua gau ccc aua acu gga gca acg cgu gau      6459
Phe Ala Phe Ile Arg Tyr Ile Asp Pro Ile Thr Gly Ala Thr Arg Asp
        2095                2100                2105

gag agu ccu uug aca gau gug gaa uua gug caa gcu cau uuc gga gaa      6507
Glu Ser Pro Leu Thr Asp Val Glu Leu Val Gln Ala His Phe Gly Glu
    2110                2115                2120

auc aga gac aaa aug cua gac gag ggc cuc auc gau agg caa cac auc      6555
Ile Arg Asp Lys Met Leu Asp Glu Gly Leu Ile Asp Arg Gln His Ile
2125                2130                2135                2140

uua aau aaa cca ggu uug aca gca uac uua guu aag gac ggg guu aag      6603
Leu Asn Lys Pro Gly Leu Thr Ala Tyr Leu Val Lys Asp Gly Val Lys
                2145                2150                2155

ucc auc aug aaa gua gau uug caa cca cac aau ccu cua cuc aua ugc      6651
Ser Ile Met Lys Val Asp Leu Gln Pro His Asn Pro Leu Leu Ile Cys
            2160                2165                2170

aaa aac aaa gcg aca aua gca ggg uuu ccu gag aag gag uuu guu uug      6699
Lys Asn Lys Ala Thr Ile Ala Gly Phe Pro Glu Lys Glu Phe Val Leu
        2175                2180                2185

cga caa acg gac aaa gca uau gaa gua agu aga gag gaa cua cca gaa      6747
Arg Gln Thr Asp Lys Ala Tyr Glu Val Ser Arg Glu Glu Leu Pro Glu
    2190                2195                2200

cgg aau gaa gac guu ucu uuu gaa gga gcc uca agu gug aag gga uug      6795
Arg Asn Glu Asp Val Ser Phe Glu Gly Ala Ser Ser Val Lys Gly Leu
2205                2210                2215                2220

cgc gau uac aau ggu gua gcc agc gcu auu ugc caa cuc aca aac aac      6843
Arg Asp Tyr Asn Gly Val Ala Ser Ala Ile Cys Gln Leu Thr Asn Asn
                2225                2230                2235

uca aau ggu cgg ucc acc aca acu uau ggg guu ggc uuu ggc uca uac      6891
Ser Asn Gly Arg Ser Thr Thr Thr Tyr Gly Val Gly Phe Gly Ser Tyr
            2240                2245                2250

auc aua guu aau agg cac uug uuu aaa gaa aau aau ggg aau uua uug      6939
Ile Ile Val Asn Arg His Leu Phe Lys Glu Asn Asn Gly Asn Leu Leu
        2255                2260                2265

auc aaa ucg acg cau gga aau uuc aau auc agg aac ucc aag caa auu      6987
Ile Lys Ser Thr His Gly Asn Phe Asn Ile Arg Asn Ser Lys Gln Ile
    2270                2275                2280

aaa guc guc gga gug gag gau agg gau auu gcc auu cuu caa aug ccu      7035
Lys Val Val Gly Val Glu Asp Arg Asp Ile Ala Ile Leu Gln Met Pro
2285                2290                2295                2300

aaa gac uuc cca ccc uuu gca cag agg uua cga uuu aga aau cca aua      7083
Lys Asp Phe Pro Pro Phe Ala Gln Arg Leu Arg Phe Arg Asn Pro Ile
                2305                2310                2315

gug ggu gaa uca auu ugu cuu guu gga aau acg uuc caa gaa aag uac      7131
Val Gly Glu Ser Ile Cys Leu Val Gly Asn Thr Phe Gln Glu Lys Tyr
            2320                2325                2330
```

-continued

```
aau gca agc auc guu ucu gag aca agc aaa aca uuc cca cga guu gaa      7179
Asn Ala Ser Ile Val Ser Glu Thr Ser Lys Thr Phe Pro Arg Val Glu
        2335                2340                2345

ggu agu uuu ugg aaa cau ugg auu aau aca acg gaa gga cau ugu gga      7227
Gly Ser Phe Trp Lys His Trp Ile Asn Thr Thr Glu Gly His Cys Gly
    2350                2355                2360

uug ccu uua guu agu guc acu gau gga uuu auu gua gga aua cau agu      7275
Leu Pro Leu Val Ser Val Thr Asp Gly Phe Ile Val Gly Ile His Ser
2365                2370                2375                2380

uua aug agu cau aag uac gau cau aau uau uuc ucg aac uuu gac gac      7323
Leu Met Ser His Lys Tyr Asp His Asn Tyr Phe Ser Asn Phe Asp Asp
                2385                2390                2395

gcg uuu gaa ggc gau uau auu aac aag uug aag gaa cug aaa ugg gag      7371
Ala Phe Glu Gly Asp Tyr Ile Asn Lys Leu Lys Glu Leu Lys Trp Glu
            2400                2405                2410

cag aau ugg acu uac aac guu aau acu guu agu ugg ggc aac aug aaa      7419
Gln Asn Trp Thr Tyr Asn Val Asn Thr Val Ser Trp Gly Asn Met Lys
        2415                2420                2425

cuu cag gau agu gcu cca ugc aaa gaa uuc aaa aca acu aag uug auu      7467
Leu Gln Asp Ser Ala Pro Cys Lys Glu Phe Lys Thr Thr Lys Leu Ile
    2430                2435                2440

agc gac uua ugc acg gaa ccu gug ugc gcu cag agu agc aau caa guu      7515
Ser Asp Leu Cys Thr Glu Pro Val Cys Ala Gln Ser Ser Asn Gln Val
2445                2450                2455                2460

aga ugg uua uau aau cag cuu gaa gga aau uug aaa gcg guu gca acu      7563
Arg Trp Leu Tyr Asn Gln Leu Glu Gly Asn Leu Lys Ala Val Ala Thr
                2465                2470                2475

auu ccc aau aac uuu guu aca aag cac auu gug aaa gga cga ugu aaa      7611
Ile Pro Asn Asn Phe Val Thr Lys His Ile Val Lys Gly Arg Cys Lys
            2480                2485                2490

uug uuu gaa uug uau cug caa acu cgu agu gaa gcg aau gag uuc uuu      7659
Leu Phe Glu Leu Tyr Leu Gln Thr Arg Ser Glu Ala Asn Glu Phe Phe
        2495                2500                2505

aaa cca cug aug ggu uuc uau ggg aag agc ggu cuc aac aag gaa gca      7707
Lys Pro Leu Met Gly Phe Tyr Gly Lys Ser Gly Leu Asn Lys Glu Ala
    2510                2515                2520

uac auu aag gac cua uuu aaa uac uca uca gaa aua cca auu ggg gag      7755
Tyr Ile Lys Asp Leu Phe Lys Tyr Ser Ser Glu Ile Pro Ile Gly Glu
2525                2530                2535                2540

guc gac acu gag aga uuu gaa gau gca guu ggg caa guc auc gaa auu      7803
Val Asp Thr Glu Arg Phe Glu Asp Ala Val Gly Gln Val Ile Glu Ile
                2545                2550                2555

aug aug caa ugg aac uuu agg gaa ugc aag uau auc acc gau ugu gac      7851
Met Met Gln Trp Asn Phe Arg Glu Cys Lys Tyr Ile Thr Asp Cys Asp
            2560                2565                2570

cag auc uuu gaa uca uug aac aug aaa gcg gca guc ggu gcg uug uac      7899
Gln Ile Phe Glu Ser Leu Asn Met Lys Ala Ala Val Gly Ala Leu Tyr
        2575                2580                2585

agu ggu aag aaa aag gcg uac uuc gaa aau ucc aca uuu gau gau cga      7947
Ser Gly Lys Lys Lys Ala Tyr Phe Glu Asn Ser Thr Phe Asp Asp Arg
    2590                2595                2600

aau cau uug cua cag cuu agu ugu cuc cga uua uuc aag ggu gau uug      7995
Asn His Leu Leu Gln Leu Ser Cys Leu Arg Leu Phe Lys Gly Asp Leu
2605                2610                2615                2620

gga auu ugg aau gga agu cuu aaa gcu gaa uua aga cca auu gaa aag      8043
Gly Ile Trp Asn Gly Ser Leu Lys Ala Glu Leu Arg Pro Ile Glu Lys
                2625                2630                2635

guu gaa gca aac aaa acg cga aca uuc aca gca gcu cca auu gaa acu      8091
Val Glu Ala Asn Lys Thr Arg Thr Phe Thr Ala Ala Pro Ile Glu Thr
            2640                2645                2650
```

-continued

```
uua cuu ggc gga aag guu ugc guc gau gau uuc aac aac caa uuu uau     8139
Leu Leu Gly Gly Lys Val Cys Val Asp Asp Phe Asn Asn Gln Phe Tyr
        2655                2660                2665

gau cuu aau aug aaa ugc cca ugg aca guc ggg aug acu aag uuu uau     8187
Asp Leu Asn Met Lys Cys Pro Trp Thr Val Gly Met Thr Lys Phe Tyr
    2670                2675                2680

ugc gga ugg aau gau cuu cua ggu aaa cuu ccu gau ggu ugg aua uac     8235
Cys Gly Trp Asn Asp Leu Leu Gly Lys Leu Pro Asp Gly Trp Ile Tyr
2685                2690                2695                2700

cgc gau gcu gac gga uca cga uuu gac agu ucu cuu aca cca uac uug     8283
Arg Asp Ala Asp Gly Ser Arg Phe Asp Ser Ser Leu Thr Pro Tyr Leu
                2705                2710                2715

cug aau gca gug cuc ggg auu agg gag uuu uuc aug gaa gau ugg gac     8331
Leu Asn Ala Val Leu Gly Ile Arg Glu Phe Phe Met Glu Asp Trp Asp
            2720                2725                2730

aua ggc gug cag aug cuu cga aau uug cac acu gaa aua auu uac acc     8379
Ile Gly Val Gln Met Leu Arg Asn Leu His Thr Glu Ile Ile Tyr Thr
        2735                2740                2745

ccc auu gca aca ccu gau gga aca guc guc aaa aag uuu cga gga aau     8427
Pro Ile Ala Thr Pro Asp Gly Thr Val Val Lys Lys Phe Arg Gly Asn
    2750                2755                2760

aau agu ggu caa ccg uca aca guc gua gau aac aca uug aug guc ugu     8475
Asn Ser Gly Gln Pro Ser Thr Val Val Asp Asn Thr Leu Met Val Cys
2765                2770                2775                2780

auu ugu gug cag uau agu uua auu aug aau agu gua aag uuu gag aau     8523
Ile Cys Val Gln Tyr Ser Leu Ile Met Asn Ser Val Lys Phe Glu Asn
                2785                2790                2795

cag gau gau guc ugc agg uau uuc guu aac ggu gau gau uua uug cuu     8571
Gln Asp Asp Val Cys Arg Tyr Phe Val Asn Gly Asp Asp Leu Leu Leu
            2800                2805                2810

gca auc aau cca aaa uuu aua cac auc cua gau ucu uuu aaa guu cau     8619
Ala Ile Asn Pro Lys Phe Ile His Ile Leu Asp Ser Phe Lys Val His
        2815                2820                2825

uuu gcu aau uua ggu uua gac uac gau uuc ucu cau cga acg aaa gac     8667
Phe Ala Asn Leu Gly Leu Asp Tyr Asp Phe Ser His Arg Thr Lys Asp
    2830                2835                2840

aaa gga gaa cuu ugg uuu aug ucu cac aaa gga guu aaa uua aau gac     8715
Lys Gly Glu Leu Trp Phe Met Ser His Lys Gly Val Lys Leu Asn Asp
2845                2850                2855                2860

aug uau auu cca aag cug gag cca gag agg guu guc uca aua cuu gag     8763
Met Tyr Ile Pro Lys Leu Glu Pro Glu Arg Val Val Ser Ile Leu Glu
                2865                2870                2875

ugg gau aga agu gua aaa cca gaa cac aga uua gaa gcg auu ugc gcu     8811
Trp Asp Arg Ser Val Lys Pro Glu His Arg Leu Glu Ala Ile Cys Ala
            2880                2885                2890

ucg aug auu gaa gca ugg ggu uac ccu agg uua auc cac gaa auu cga     8859
Ser Met Ile Glu Ala Trp Gly Tyr Pro Arg Leu Ile His Glu Ile Arg
        2895                2900                2905

aaa uuu uau gcu ugg guu cug gaa caa gca cca uac aau cau cuc gca     8907
Lys Phe Tyr Ala Trp Val Leu Glu Gln Ala Pro Tyr Asn His Leu Ala
    2910                2915                2920

ucu gag gga aag gca cca uac auu ucg gaa aca gcg cuc aaa aga cuu     8955
Ser Glu Gly Lys Ala Pro Tyr Ile Ser Glu Thr Ala Leu Lys Arg Leu
2925                2930                2935                2940

uac aca ugc gaa gaa gga agu gcu gau gaa auc aug uca uac uua gag     9003
Tyr Thr Cys Glu Glu Gly Ser Ala Asp Glu Ile Met Ser Tyr Leu Glu
                2945                2950                2955

aug ugu gca agu gau uug aac gag gau gag uac uuu gau gau gaa gau     9051
Met Cys Ala Ser Asp Leu Asn Glu Asp Glu Tyr Phe Asp Asp Glu Asp
```

-continued

```
        2960                2965                2970

guu ucu cac cag ucc gcu cuu gau gcu ggc aaa ccc aca gca gaa aac      9099
Val Ser His Gln Ser Ala Leu Asp Ala Gly Lys Pro Thr Ala Glu Asn
        2975                2980                2985

aag aaa gac gau gaa gag aga aag aau aaa gaa gaa aag cag gaa aau      9147
Lys Lys Asp Asp Glu Glu Arg Lys Asn Lys Glu Glu Lys Gln Glu Asn
    2990                2995                3000

aaa aac aaa aau aaa gaa guc gag aag aaa cau gag aaa acu ucg aau      9195
Lys Asn Lys Asn Lys Glu Val Glu Lys Lys His Glu Lys Thr Ser Asn
3005                3010                3015                3020

agc gca ucu ggu gcu auu guu uca aac aac gaa aaa gac aag gau guc      9243
Ser Ala Ser Gly Ala Ile Val Ser Asn Asn Glu Lys Asp Lys Asp Val
                3025                3030                3035

gau gua gga uca agu gga ucu uuc auc aua cca cga auu aaa ucg aua      9291
Asp Val Gly Ser Ser Gly Ser Phe Ile Ile Pro Arg Ile Lys Ser Ile
            3040                3045                3050

ucc aau aaa cuc aca aug cca aaa gug aaa ggg aaa gga auu uua aau      9339
Ser Asn Lys Leu Thr Met Pro Lys Val Lys Gly Lys Gly Ile Leu Asn
        3055                3060                3065

uug gag uuc cuu uua caa uac aca cca gau caa gug gac auu uca aau      9387
Leu Glu Phe Leu Leu Gln Tyr Thr Pro Asp Gln Val Asp Ile Ser Asn
    3070                3075                3080

acc agg gca agu auu uca cag uuu aau aca ugg uac aac gcu gug aag      9435
Thr Arg Ala Ser Ile Ser Gln Phe Asn Thr Trp Tyr Asn Ala Val Lys
3085                3090                3095                3100

gaa ucc uau ggu gug ucu gau gaa gaa aug gga aua auu uug aau gga      9483
Glu Ser Tyr Gly Val Ser Asp Glu Glu Met Gly Ile Ile Leu Asn Gly
                3105                3110                3115

uua aug guu ugg ugu auu gaa aau gga aca ucu cca aac auu aau ggc      9531
Leu Met Val Trp Cys Ile Glu Asn Gly Thr Ser Pro Asn Ile Asn Gly
            3120                3125                3130

aug ugg uuu aug aug caa ggg gaa gaa caa auc gaa uac ccc cuu caa      9579
Met Trp Phe Met Met Gln Gly Glu Glu Gln Ile Glu Tyr Pro Leu Gln
        3135                3140                3145

cca aua gug gaa aac gca aaa ccc acu uug cgu cag auu aug gcu cac      9627
Pro Ile Val Glu Asn Ala Lys Pro Thr Leu Arg Gln Ile Met Ala His
    3150                3155                3160

uuu agc aau guu gcu gaa gca uac auc gaa aag aga aau uau gag aag      9675
Phe Ser Asn Val Ala Glu Ala Tyr Ile Glu Lys Arg Asn Tyr Glu Lys
3165                3170                3175                3180

cca uau aug ccg agg uac ggu auu caa cgg aac cuc acc gac aug agu      9723
Pro Tyr Met Pro Arg Tyr Gly Ile Gln Arg Asn Leu Thr Asp Met Ser
                3185                3190                3195

uug gcg cga uau gcu uuu gau uuc uau gaa aug aca uca agg acg cca      9771
Leu Ala Arg Tyr Ala Phe Asp Phe Tyr Glu Met Thr Ser Arg Thr Pro
            3200                3205                3210

gcu cgg gcc cgg gaa gcc cac auc cag aug aaa gcu gca gca uug cga      9819
Ala Arg Ala Arg Glu Ala His Ile Gln Met Lys Ala Ala Ala Leu Arg
        3215                3220                3225

gau gcg aau aau aag aug uuu gga cug gau gga aaa guc gga aau gcg      9867
Asp Ala Asn Asn Lys Met Phe Gly Leu Asp Gly Lys Val Gly Asn Ala
    3230                3235                3240

acu gag aac acg gag cgc cac acc gca gac gau guu aac cau aac acu      9915
Thr Glu Asn Thr Glu Arg His Thr Ala Asp Asp Val Asn His Asn Thr
3245                3250                3255                3260

cau gca uuc acc ggc guu cga uau uau uagauauuua ccuaagcaua            9962
His Ala Phe Thr Gly Val Arg Tyr Tyr
                3265

guuuuaucua guaucuuuua aaucgcauua gcuuuacuuu cuagcacgcg uuagugaggu  10022
```

-continued

```
uuuaccuccu auuaucuaug ugucagugag gguagcccuc gugugaucuc uuagaaagua  10082

uugucccaag cugcaguggc ugguuguuca uagcaugagu ggcucaugga ccuucagccu  10142

aagcaaggag ggn                                                     10155


<210> SEQ ID NO 2
<211> LENGTH: 3269
<212> TYPE: PRT
<213> ORGANISM: Papaya Leaf-Distortion Mosaic Virus

<400> SEQUENCE: 2

Met Ser Ile Val Ile Gly Asp Phe Ser Ile Pro Leu Ile Cys Arg Thr
1               5                   10                  15

Glu Gln Ile Glu Cys Val Arg Leu Val Pro Gly Thr Arg Val Glu Glu
            20                  25                  30

Val Lys Thr Ile Lys Lys Val Leu Lys Thr His Tyr Gln Glu Ile Thr
        35                  40                  45

Leu Gly Cys Thr Asp Arg Cys Ala Gly Leu Ser Ala Tyr Thr Lys Thr
    50                  55                  60

Ser Leu Lys Arg Ala Ile Lys Glu Lys Asp Leu Thr Ala Ser Gly Ser
65                  70                  75                  80

Cys Phe His Cys Gly Leu Arg Ala Gln Ile Gly Glu Gly Arg Lys Arg
                85                  90                  95

Val Glu Leu Ala Pro Ile Ser Val Met Glu Asp Val Glu Thr Val Glu
            100                 105                 110

Gln Val Leu Val Pro Cys Met Val Glu Glu Lys Tyr Tyr Lys Glu Val
        115                 120                 125

Ser Asn Phe Gln Lys Ala Thr Leu Ile Asp Lys Pro Lys Leu Thr Ile
    130                 135                 140

Ala Pro Val Leu Met Ala Gln Pro Ala Gln Val Pro Arg Pro Ala Val
145                 150                 155                 160

Phe Asn Glu Ile Arg Lys Val His Glu Glu Met Lys Ser Gln Thr Ser
                165                 170                 175

Glu Asn Lys Val Leu Glu Glu Glu Thr Gln Cys Ala Ser Asp Ala Ala
            180                 185                 190

Leu His His Leu Asp Asp Val His Ala Cys Arg Ala Arg Ala Gln Val
        195                 200                 205

Gly Ile Glu Arg Ile Leu Ala Arg His Ala Arg His Arg Ile Glu Ala
    210                 215                 220

Arg Gln Gln Val Glu Glu Glu Gln Ser Glu Ala Leu Ala Ala Phe Glu
225                 230                 235                 240

Ser Phe Phe Asn Gln Thr His Arg Glu Asp Arg Tyr Glu Gly Lys Val
                245                 250                 255

Leu Thr Ile Arg Asn Gly Ile Thr Gly Trp Phe Glu Pro Asn Arg Asn
            260                 265                 270

Asp Ile Lys Asn Ala Ala Arg Arg Arg Lys Arg Ala Asn Lys Lys Ile
        275                 280                 285

Pro Phe Val Ala Arg Glu Asn Asp Val Ala Arg Ile Glu Thr His Glu
    290                 295                 300

Pro Asn Val Lys Glu Glu Thr Lys Asp Val Glu Glu Ala Thr Asp Thr
305                 310                 315                 320

Tyr Thr Phe Lys Lys Gln Arg Asn Asp Lys Lys Arg Val Leu Lys Glu
                325                 330                 335

Asn Val Ser Leu Ser Met Ala Arg Ile Asn Glu Leu Val Arg Cys Val
```

-continued

```
        340                 345                 350

Thr Lys Leu Cys Arg Lys Asp Ser Lys Glu Leu Glu Phe Ile Gly Lys
            355                 360                 365

Arg Gly Ser Leu Arg Val Gln Cys Thr Lys Asn Cys Gly Ser Arg Val
    370                 375                 380

Ile Leu Arg His Leu Arg Gly Glu Leu Arg Arg Lys Asp Cys Tyr Trp
385                 390                 395                 400

Asp Arg Ile Ile Glu Asn Phe Phe Glu Ile Ala Ala Ala Lys Leu Gln
                405                 410                 415

Asn Lys Asn Leu Asn Asn Asn Glu Ser Val Arg Arg Gly His Ser Gly
            420                 425                 430

His Ile Ile Gln Tyr Asp Lys Phe Arg Gly Leu Ser Gly Arg His Phe
        435                 440                 445

Gly Ser Tyr Ile Ile Val Arg Gly Ser Met Asp Gly Arg Ile Ile Asp
    450                 455                 460

Ala Arg Ser Lys Ile Thr His Ser Val Met Ile Asn Met Thr His Tyr
465                 470                 475                 480

Ser Asp Ala Gly Leu Ser Phe Trp Lys Gly Phe Asp Arg Gln Phe Ile
                485                 490                 495

Asp Ile Arg Asp Arg Pro Lys Asn Ala His Glu Cys Lys Ala Thr Ile
            500                 505                 510

Asn Val Glu Glu Cys Gly Glu Met Ala Ala Ile Val Asn Gln Leu Leu
        515                 520                 525

Phe Pro Met Trp Lys Ile Thr Cys Thr Gln Cys Gly Glu Leu Leu Glu
    530                 535                 540

Met Leu Ser Gln Glu Glu Glu Leu Glu Ser Phe Arg Arg Lys Arg Ser
545                 550                 555                 560

Gln Leu Ala Ser Lys Leu Ser Ser Leu His Ile Lys Phe Pro Tyr Val
                565                 570                 575

Asp His Phe Leu Asn Arg Tyr Glu Asn Ser Leu Asn Arg Met Asn Thr
            580                 585                 590

Asn Phe Asp Ala His Lys Gln Ile Ala Gln Ile Ile Gly Ser Arg Lys
        595                 600                 605

Glu Ile Pro Phe Ser Asn Leu Glu His Leu Asn Glu Leu Leu Ile Lys
    610                 615                 620

Ser Asp Lys Leu Val Ser Glu Asp Phe Tyr Glu Met Ser Gln Cys Leu
625                 630                 635                 640

Leu Glu Leu Thr Arg Trp His Lys Asn Arg Ser Asp Ser Phe Lys Lys
                645                 650                 655

Gly Glu Ile His His Phe Arg Asn Lys Met Ser Gly Lys Ala Gln Phe
            660                 665                 670

Asn Phe Ala Leu Met Cys Asp Asn Gln Leu Asp Lys Asn Gly Asn Phe
        675                 680                 685

Val Trp Gly Glu Arg Gly Tyr His Ala Lys Arg Phe Phe Leu Asn Phe
    690                 695                 700

Phe Glu Lys Val Asp Ser Thr Asp Gly Tyr Lys Lys His Ile Met Arg
705                 710                 715                 720

Val Asn Pro Asn Gly Thr Arg Gln Thr Ala Ile Gly Lys Leu Ile Leu
                725                 730                 735

Ser Thr Asp Pro Ser Thr Leu Arg Gln Gln Met Lys Gly Ser Pro Ile
            740                 745                 750

Thr Arg Val Pro Val Gly Lys Tyr Cys Thr Ser Lys Arg Asp Gly Cys
        755                 760                 765
```

-continued

```
Tyr Val Tyr Pro Ala Cys Cys Val Thr Met Glu Asp Gly Thr Pro Leu
    770                 775                 780

Phe Ser Asp Ile Lys Met Pro Thr Lys Asn His Leu Val Ile Gly Asn
785                 790                 795                 800

Ser Gly Asp Pro Lys Tyr Val Asp Val Pro Ser Ser Ser Ser Asp Met
                805                 810                 815

Ile Val Ala Lys Glu Gly Tyr Cys Tyr Leu Asn Ile Phe Leu Ala Met
            820                 825                 830

Leu Leu Asn Val Asn Glu Ser Glu Ser Lys Ser Phe Thr Lys Lys Val
        835                 840                 845

Arg Asp Ile Ile Val Pro Arg Leu Gly Gln Trp Pro Ser Leu Ile Asp
    850                 855                 860

Val Ala Thr Glu Cys Tyr Phe Leu Ser Ala Phe His Pro Glu Thr Lys
865                 870                 875                 880

Asn Ala Glu Leu Pro Arg Ile Leu Val Asp His Thr Ser Lys Cys Met
                885                 890                 895

His Val Ile Asp Ser Tyr Gly Ser Leu Asp Thr Gln Phe His Val Leu
            900                 905                 910

Lys Ala Asn Thr Val Ser Gln Leu Ile Lys Phe Ala Asp Asn Asp Leu
        915                 920                 925

Asp Ser Glu Leu Lys His Tyr Leu Val Gly Gly Asp Leu His Ser Lys
    930                 935                 940

Gln Ala Pro Gln Cys Ser Ile Lys Leu Leu Cys Lys Cys Ile Tyr Arg
945                 950                 955                 960

Pro Lys Leu Met Arg Gln Cys Ile Glu Glu Glu Pro Phe Leu Leu Ile
                965                 970                 975

Leu Ala Cys Ile Ser Pro Gly Val Leu Leu Ala Leu Tyr Asn Ser Gln
            980                 985                 990

His Leu Glu Leu Ala Leu Lys Tyr Trp Met Ser Lys Gln Gln Ser Val
        995                 1000                1005

Ala Ala Leu Phe Ala Met Ile His Gly Leu Ala Ala Lys Val Thr Val
    1010                1015                1020

Ala Gln Thr Leu Asn Glu Gln Arg Leu Ile Leu Glu Arg Gly Ala Arg
1025                1030                1035                1040

Asn Leu Ile Ser Val Met Glu Thr Ile His Met Thr Ser His Ser Tyr
                1045                1050                1055

Gln Pro Ala Leu Leu Gln Leu Gln Val Met Ala Asn Arg Arg Asp Met
            1060                1065                1070

Asn Ser Thr Leu Asp Leu Ala Gly Phe Ser Ile Leu Gln Ser Glu Asp
        1075                1080                1085

Ser Met Tyr Trp Met Glu Lys Ser Tyr Leu Met Glu Leu Glu Asp Ser
    1090                1095                1100

Trp Asn Asp Leu Lys Trp Leu Glu Lys Leu Gln Glu Met Trp Arg Leu
1105                1110                1115                1120

Ser Lys Tyr Ser Ile Ser Gly Ile Ser Gln Leu Ser Met Lys Gly Ala
                1125                1130                1135

Thr Asp Leu Gly Gly Arg Tyr Ser Val Ser Ala Lys Gln Phe Ile Thr
            1140                1145                1150

Ser Val Met Lys Pro Val Lys Lys Ser Cys Val Lys Ala Arg Asp Thr
        1155                1160                1165

Cys Lys Glu Val Ile Ile Asn Thr Thr Ser Trp Thr Phe Arg Ala Thr
    1170                1175                1180
```

-continued

```
Phe Ser Leu Cys Arg Trp Cys Leu Pro Asp Cys Leu Lys Phe Ile Asn
1185                1190                1195                1200

Met Leu Ile Val Ile Ser Leu Ile Leu Ser Ile Trp His Ser Ala Asn
                1205                1210                1215

Ser Ile Ser Phe Asp Tyr Ala Gln Met Lys Arg Glu Lys Gln Val Asn
            1220                1225                1230

Ile Glu Lys Val Leu Met Asn Asn Leu Val Ala Leu His Lys Glu Gln
        1235                1240                1245

Ile Lys Ile Asn Pro Asp Leu Thr Lys Glu Glu Phe Lys Glu Tyr Ile
    1250                1255                1260

Ala Arg Ser Arg Pro Glu Leu Ile Ala Leu Val Asn Lys Glu Leu Gln
1265                1270                1275                1280

Glu Glu Val Asp His Gln Ala Lys Arg Lys Gly Glu Gln Asn Leu Glu
                1285                1290                1295

Lys Ile Ile Ala Phe Val Ala Leu Val Met Met Ile Phe Asp Ser Glu
            1300                1305                1310

Lys Ser Asp Cys Val Tyr Lys Thr Leu Asn Lys Leu Arg Asn Leu Val
        1315                1320                1325

Ala Thr Cys Asp Glu Pro Val Ala His Gln Ser Leu Asp Asp Ile Gln
    1330                1335                1340

Asp Ile Leu Thr Asp Lys Glu Thr Thr Ile Asp Phe Asp Leu Asp Cys
1345                1350                1355                1360

Glu Gly Ser Lys Val Thr Glu Phe Lys Glu Met Asn Phe Ala Ala Trp
                1365                1370                1375

Trp Glu Lys Gln Leu Gln Cys Asp Arg Val Val Pro His Tyr Arg Thr
            1380                1385                1390

Thr Gly Lys Phe Ile Glu Phe Thr Arg Glu Ser Cys Val Ser Val Ser
        1395                1400                1405

Asn Thr Ile Ser His Ala Pro Glu Lys Glu Trp Ile Val Arg Gly Gly
    1410                1415                1420

Val Gly Ser Gly Lys Ser Thr Gly Leu Pro Phe Ala Leu Ser Ser Lys
1425                1430                1435                1440

Gly Ala Val Leu Met Leu Glu Pro Thr Arg Pro Leu Ala Glu Asn Val
                1445                1450                1455

Ser Arg Gln Leu Arg Gln His Pro Phe Tyr Ala Asn Pro Thr Leu Arg
            1460                1465                1470

Met Arg Gly Met Ser Ser Phe Gly Ser Ser Asn Ile Cys Ile Met Thr
        1475                1480                1485

Ser Gly Phe Ala Phe Asn Tyr Phe Ala Asn Asn Pro Leu Lys Leu Ser
    1490                1495                1500

Asp Phe Glu Phe Val Ile Ile Asp Glu Cys His Val Leu Asp Ser Asn
1505                1510                1515                1520

Ala Met Ala Phe Val Cys Leu Leu Lys Glu His Asn Tyr Asp Gly Lys
                1525                1530                1535

Leu Leu Lys Val Ser Ala Thr Pro Gln Gly Arg Glu Cys Glu Phe His
            1540                1545                1550

Thr Gln His Pro Val Ser Ile His Ile Glu Glu Gln Leu Ser Phe Gln
        1555                1560                1565

Ala Phe Cys Glu Ala Gln Gly Thr Gly Ser Ala Arg Asp Val Ile Asn
    1570                1575                1580

Lys Gly Asp Asn Ile Leu Val Tyr Val Ala Ser Tyr Asn Glu Val Asp
1585                1590                1595                1600

Gln Leu Ser Lys Met Leu Gly Asp Lys Gly Tyr Leu Val Thr Lys Val
```

-continued

```
            1605                1610                1615

Asp Gly Arg Thr Met Lys Ile Gly Ser Thr Asp Ile Val Thr Lys Gly
            1620                1625                1630

Ser Ser Gln Lys Lys His Phe Ile Val Ala Thr Asn Ile Ile Glu Asn
        1635                1640                1645

Gly Val Thr Leu Asp Val Asp Val Val Val Asp Phe Gly Leu Lys Val
    1650                1655                1660

Thr Ala Glu Ile Asp Tyr Asp Asn Arg Cys Val Asn Tyr Thr Lys Thr
1665                1670                1675                1680

Ser Ile Ser Tyr Gly Glu Arg Ile Gln Arg Leu Gly Arg Val Gly Arg
                1685                1690                1695

His Lys Lys Gly His Ala Met Arg Ile Gly Thr Thr Ile Lys Gly Leu
            1700                1705                1710

Ile Glu Ile Pro Ser Leu Val Ala Thr Gln Ala Ala Phe Gln Cys Phe
        1715                1720                1725

Thr Tyr Gly Leu Pro Val Met Thr Gln Gly Val Ser Val Asn Ser Leu
    1730                1735                1740

Ser Asn Cys Thr Val Arg Gln Ala Arg Val Met Ser Arg Phe Glu Leu
1745                1750                1755                1760

Pro Pro Tyr Phe Met Ala Ser Leu Val Tyr His Asp Gly Ser Met His
                1765                1770                1775

Pro Glu Ile His Lys His Leu Ile Pro Tyr Lys Leu Asp Glu Ser Glu
            1780                1785                1790

Ile Gln Leu Ser Ala Met Ala Phe Asn Phe Thr Val Thr Ser Ile Trp
        1795                1800                1805

Leu Asp Cys Lys Phe Tyr Asp Ser Ile Gly Ile His Leu Asp Leu Pro
    1810                1815                1820

Arg Glu Ala Lys Ile Pro Phe His Cys Arg Glu Phe Pro Asp Met Lys
1825                1830                1835                1840

Tyr Arg His Leu Trp Glu Asp Ile Leu Lys Ile Lys Ser Ile Asn Cys
                1845                1850                1855

Phe Gly Arg Met Ser Val Val Ser Ala Thr Lys Val Ala Tyr Thr Leu
            1860                1865                1870

Lys Thr Asp Ile His Ser Ile Gly Lys Thr Leu Gly Tyr Ile Asp Ala
        1875                1880                1885

Leu Leu Gln Glu Glu Tyr Arg Lys Gln His His Phe Lys Ala Met Thr
    1890                1895                1900

Ser Asn Ala Cys Ser Gly Asn Thr Phe Ser Met Leu Ser Ile Ala Asn
1905                1910                1915                1920

Ala Ile Arg Asn His Tyr Ala Lys Asp Tyr Thr Ala Gly Asn Ile Gln
                1925                1930                1935

Lys Leu Gln Ala Ala Lys Asn Gln Ile Leu Glu Phe Val Asn Leu Asn
            1940                1945                1950

Leu Asp Pro Ser Ala Lys Cys Gly Phe Gln Glu Phe Gly Ala Leu Glu
        1955                1960                1965

Leu Val Thr His Gln Ser Arg Gln Glu Ile Ser Lys Phe Leu Asn Leu
    1970                1975                1980

Arg Gly Lys Trp Asn Lys Ser Leu Ile Thr Arg Asp Ile Leu Val Leu
1985                1990                1995                2000

Leu Gly Val Thr Ile Gly Gly Phe Trp Met Ile Trp Asp Lys Phe Lys
                2005                2010                2015

Ser Asn Ile Glu Glu Val His His Glu Gly Lys Arg Lys Thr Gln Lys
            2020                2025                2030
```

-continued

```
Leu Lys Phe Arg Asp Ala Arg Asp Lys Lys Met Gly Arg Glu Val Tyr
        2035                2040                2045

Gly Asp Asp Gly Thr Ile Glu His Tyr Phe Gly Ser Ala Tyr Val Lys
    2050                2055                2060

Arg Gly Ala Val Lys Gly Gln Lys Arg Gly Met Gly Glu Lys Ser Arg
2065                2070                2075                2080

Arg Phe Val Ser Met Tyr Gly Val Asn Leu Glu Asp Phe Ala Phe Ile
                2085                2090                2095

Arg Tyr Ile Asp Pro Ile Thr Gly Ala Thr Arg Asp Glu Ser Pro Leu
            2100                2105                2110

Thr Asp Val Glu Leu Val Gln Ala His Phe Gly Glu Ile Arg Asp Lys
        2115                2120                2125

Met Leu Asp Glu Gly Leu Ile Asp Arg Gln His Ile Leu Asn Lys Pro
    2130                2135                2140

Gly Leu Thr Ala Tyr Leu Val Lys Asp Gly Val Lys Ser Ile Met Lys
2145                2150                2155                2160

Val Asp Leu Gln Pro His Asn Pro Leu Leu Ile Cys Lys Asn Lys Ala
                2165                2170                2175

Thr Ile Ala Gly Phe Pro Glu Lys Glu Phe Val Leu Arg Gln Thr Asp
            2180                2185                2190

Lys Ala Tyr Glu Val Ser Arg Glu Glu Leu Pro Glu Arg Asn Glu Asp
        2195                2200                2205

Val Ser Phe Glu Gly Ala Ser Ser Val Lys Gly Leu Arg Asp Tyr Asn
    2210                2215                2220

Gly Val Ala Ser Ala Ile Cys Gln Leu Thr Asn Asn Ser Asn Gly Arg
2225                2230                2235                2240

Ser Thr Thr Thr Tyr Gly Val Gly Phe Gly Ser Tyr Ile Ile Val Asn
                2245                2250                2255

Arg His Leu Phe Lys Glu Asn Asn Gly Asn Leu Leu Ile Lys Ser Thr
            2260                2265                2270

His Gly Asn Phe Asn Ile Arg Asn Ser Lys Gln Ile Lys Val Val Gly
        2275                2280                2285

Val Glu Asp Arg Asp Ile Ala Ile Leu Gln Met Pro Lys Asp Phe Pro
    2290                2295                2300

Pro Phe Ala Gln Arg Leu Arg Phe Arg Asn Pro Ile Val Gly Glu Ser
2305                2310                2315                2320

Ile Cys Leu Val Gly Asn Thr Phe Gln Glu Lys Tyr Asn Ala Ser Ile
                2325                2330                2335

Val Ser Glu Thr Ser Lys Thr Phe Pro Arg Val Glu Gly Ser Phe Trp
            2340                2345                2350

Lys His Trp Ile Asn Thr Thr Glu Gly His Cys Gly Leu Pro Leu Val
        2355                2360                2365

Ser Val Thr Asp Gly Phe Ile Val Gly Ile His Ser Leu Met Ser His
    2370                2375                2380

Lys Tyr Asp His Asn Tyr Phe Ser Asn Phe Asp Asp Ala Phe Glu Gly
2385                2390                2395                2400

Asp Tyr Ile Asn Lys Leu Lys Glu Leu Lys Trp Glu Gln Asn Trp Thr
                2405                2410                2415

Tyr Asn Val Asn Thr Val Ser Trp Gly Asn Met Lys Leu Gln Asp Ser
            2420                2425                2430

Ala Pro Cys Lys Glu Phe Lys Thr Thr Lys Leu Ile Ser Asp Leu Cys
        2435                2440                2445
```

-continued

```
Thr Glu Pro Val Cys Ala Gln Ser Ser Asn Gln Val Arg Trp Leu Tyr
    2450                2455                2460

Asn Gln Leu Glu Gly Asn Leu Lys Ala Val Ala Thr Ile Pro Asn Asn
2465                2470                2475                2480

Phe Val Thr Lys His Ile Val Lys Gly Arg Cys Lys Leu Phe Glu Leu
                2485                2490                2495

Tyr Leu Gln Thr Arg Ser Glu Ala Asn Glu Phe Phe Lys Pro Leu Met
            2500                2505                2510

Gly Phe Tyr Gly Lys Ser Gly Leu Asn Lys Glu Ala Tyr Ile Lys Asp
        2515                2520                2525

Leu Phe Lys Tyr Ser Ser Glu Ile Pro Ile Gly Glu Val Asp Thr Glu
    2530                2535                2540

Arg Phe Glu Asp Ala Val Gly Gln Val Ile Glu Ile Met Met Gln Trp
2545                2550                2555                2560

Asn Phe Arg Glu Cys Lys Tyr Ile Thr Asp Cys Asp Gln Ile Phe Glu
                2565                2570                2575

Ser Leu Asn Met Lys Ala Ala Val Gly Ala Leu Tyr Ser Gly Lys Lys
            2580                2585                2590

Lys Ala Tyr Phe Glu Asn Ser Thr Phe Asp Asp Arg Asn His Leu Leu
        2595                2600                2605

Gln Leu Ser Cys Leu Arg Leu Phe Lys Gly Asp Leu Gly Ile Trp Asn
    2610                2615                2620

Gly Ser Leu Lys Ala Glu Leu Arg Pro Ile Glu Lys Val Glu Ala Asn
2625                2630                2635                2640

Lys Thr Arg Thr Phe Thr Ala Ala Pro Ile Glu Thr Leu Leu Gly Gly
                2645                2650                2655

Lys Val Cys Val Asp Asp Phe Asn Asn Gln Phe Tyr Asp Leu Asn Met
            2660                2665                2670

Lys Cys Pro Trp Thr Val Gly Met Thr Lys Phe Tyr Cys Gly Trp Asn
        2675                2680                2685

Asp Leu Leu Gly Lys Leu Pro Asp Gly Trp Ile Tyr Arg Asp Ala Asp
    2690                2695                2700

Gly Ser Arg Phe Asp Ser Ser Leu Thr Pro Tyr Leu Leu Asn Ala Val
2705                2710                2715                2720

Leu Gly Ile Arg Glu Phe Phe Met Glu Asp Trp Asp Ile Gly Val Gln
                2725                2730                2735

Met Leu Arg Asn Leu His Thr Glu Ile Ile Tyr Thr Pro Ile Ala Thr
            2740                2745                2750

Pro Asp Gly Thr Val Val Lys Lys Phe Arg Gly Asn Asn Ser Gly Gln
        2755                2760                2765

Pro Ser Thr Val Val Asp Asn Thr Leu Met Val Cys Ile Cys Val Gln
    2770                2775                2780

Tyr Ser Leu Ile Met Asn Ser Val Lys Phe Glu Asn Gln Asp Asp Val
2785                2790                2795                2800

Cys Arg Tyr Phe Val Asn Gly Asp Asp Leu Leu Leu Ala Ile Asn Pro
                2805                2810                2815

Lys Phe Ile His Ile Leu Asp Ser Phe Lys Val His Phe Ala Asn Leu
            2820                2825                2830

Gly Leu Asp Tyr Asp Phe Ser His Arg Thr Lys Asp Lys Gly Glu Leu
        2835                2840                2845

Trp Phe Met Ser His Lys Gly Val Lys Leu Asn Asp Met Tyr Ile Pro
    2850                2855                2860

Lys Leu Glu Pro Glu Arg Val Val Ser Ile Leu Glu Trp Asp Arg Ser
```

-continued

```
2865                2870                2875                2880

Val Lys Pro Glu His Arg Leu Glu Ala Ile Cys Ala Ser Met Ile Glu
                2885                2890                2895

Ala Trp Gly Tyr Pro Arg Leu Ile His Glu Ile Arg Lys Phe Tyr Ala
            2900                2905                2910

Trp Val Leu Glu Gln Ala Pro Tyr Asn His Leu Ala Ser Glu Gly Lys
        2915                2920                2925

Ala Pro Tyr Ile Ser Glu Thr Ala Leu Lys Arg Leu Tyr Thr Cys Glu
    2930                2935                2940

Glu Gly Ser Ala Asp Glu Ile Met Ser Tyr Leu Glu Met Cys Ala Ser
2945                2950                2955                2960

Asp Leu Asn Glu Asp Glu Tyr Phe Asp Asp Glu Asp Val Ser His Gln
                2965                2970                2975

Ser Ala Leu Asp Ala Gly Lys Pro Thr Ala Glu Asn Lys Lys Asp Asp
            2980                2985                2990

Glu Glu Arg Lys Asn Lys Glu Glu Lys Gln Glu Asn Lys Asn Lys Asn
        2995                3000                3005

Lys Glu Val Glu Lys Lys His Glu Lys Thr Ser Asn Ser Ala Ser Gly
    3010                3015                3020

Ala Ile Val Ser Asn Asn Glu Lys Asp Lys Asp Val Asp Val Gly Ser
3025                3030                3035                3040

Ser Gly Ser Phe Ile Ile Pro Arg Ile Lys Ser Ile Ser Asn Lys Leu
                3045                3050                3055

Thr Met Pro Lys Val Lys Gly Lys Gly Ile Leu Asn Leu Glu Phe Leu
            3060                3065                3070

Leu Gln Tyr Thr Pro Asp Gln Val Asp Ile Ser Asn Thr Arg Ala Ser
        3075                3080                3085

Ile Ser Gln Phe Asn Thr Trp Tyr Asn Ala Val Lys Glu Ser Tyr Gly
    3090                3095                3100

Val Ser Asp Glu Glu Met Gly Ile Ile Leu Asn Gly Leu Met Val Trp
3105                3110                3115                3120

Cys Ile Glu Asn Gly Thr Ser Pro Asn Ile Asn Gly Met Trp Phe Met
                3125                3130                3135

Met Gln Gly Glu Glu Gln Ile Glu Tyr Pro Leu Gln Pro Ile Val Glu
            3140                3145                3150

Asn Ala Lys Pro Thr Leu Arg Gln Ile Met Ala His Phe Ser Asn Val
        3155                3160                3165

Ala Glu Ala Tyr Ile Glu Lys Arg Asn Tyr Glu Lys Pro Tyr Met Pro
    3170                3175                3180

Arg Tyr Gly Ile Gln Arg Asn Leu Thr Asp Met Ser Leu Ala Arg Tyr
3185                3190                3195                3200

Ala Phe Asp Phe Tyr Glu Met Thr Ser Arg Thr Pro Ala Arg Ala Arg
                3205                3210                3215

Glu Ala His Ile Gln Met Lys Ala Ala Ala Leu Arg Asp Ala Asn Asn
            3220                3225                3230

Lys Met Phe Gly Leu Asp Gly Lys Val Gly Asn Ala Thr Glu Asn Thr
        3235                3240                3245

Glu Arg His Thr Ala Asp Asp Val Asn His Asn Thr His Ala Phe Thr
    3250                3255                3260

Gly Val Arg Tyr Tyr
3265
```

<210> SEQ ID NO 3

-continued

```
<211> LENGTH: 729
<212> TYPE: DNA
<213> ORGANISM: Papaya Leaf-Distortion Mosaic Virus
<220> FEATURE:
<221> NAME/KEY: CDS
<222> LOCATION: (1)..(729)

<400> SEQUENCE: 3

gga gcc tca agt gtg aag gga ttg cgc gat tac aat ggt gta gcc agc       48
Gly Ala Ser Ser Val Lys Gly Leu Arg Asp Tyr Asn Gly Val Ala Ser
1               5                   10                  15

gct att tgc caa ctc aca aac aac tca aat ggt cgg tcc acc aca act       96
Ala Ile Cys Gln Leu Thr Asn Asn Ser Asn Gly Arg Ser Thr Thr Thr
            20                  25                  30

tat ggg gtt ggc ttt ggc tca tac atc ata gtt aat agg cac ttg ttt      144
Tyr Gly Val Gly Phe Gly Ser Tyr Ile Ile Val Asn Arg His Leu Phe
        35                  40                  45

aaa gaa aat aat ggg aat tta ttg atc aaa tcg acg cat gga aat ttc      192
Lys Glu Asn Asn Gly Asn Leu Leu Ile Lys Ser Thr His Gly Asn Phe
    50                  55                  60

aat atc agg aac tcc aag caa att aaa gtc gtc gga gtg gag gat agg      240
Asn Ile Arg Asn Ser Lys Gln Ile Lys Val Val Gly Val Glu Asp Arg
65                  70                  75                  80

gat att gcc att ctt caa atg cct aaa gac ttc cca ccc ttt gca cag      288
Asp Ile Ala Ile Leu Gln Met Pro Lys Asp Phe Pro Pro Phe Ala Gln
                85                  90                  95

agg tta cga ttt aga aat cca ata gtg ggt gaa tca att tgt ctt gtt      336
Arg Leu Arg Phe Arg Asn Pro Ile Val Gly Glu Ser Ile Cys Leu Val
            100                 105                 110

gga aat acg ttc caa gaa aag tac aat gca agc atc gtt tct gag aca      384
Gly Asn Thr Phe Gln Glu Lys Tyr Asn Ala Ser Ile Val Ser Glu Thr
        115                 120                 125

agc aaa aca ttc cca cga gtt gaa ggt agt ttt tgg aaa cat tgg att      432
Ser Lys Thr Phe Pro Arg Val Glu Gly Ser Phe Trp Lys His Trp Ile
    130                 135                 140

aat aca acg gaa gga cat tgt gga ttg cct tta gtt agt gtc act gat      480
Asn Thr Thr Glu Gly His Cys Gly Leu Pro Leu Val Ser Val Thr Asp
145                 150                 155                 160

gga ttt att gta gga ata cat agt tta atg agt cat aag tac gat cat      528
Gly Phe Ile Val Gly Ile His Ser Leu Met Ser His Lys Tyr Asp His
                165                 170                 175

aat tat ttc tcg aac ttt gac gac gcg ttt gaa ggc gat tat att aac      576
Asn Tyr Phe Ser Asn Phe Asp Asp Ala Phe Glu Gly Asp Tyr Ile Asn
            180                 185                 190

aag ttg aag gaa ctg aaa tgg gag cag aat tgg act tac aac gtt aat      624
Lys Leu Lys Glu Leu Lys Trp Glu Gln Asn Trp Thr Tyr Asn Val Asn
        195                 200                 205

act gtt agt tgg ggc aac atg aaa ctt cag gat agt gct cca tgc aaa      672
Thr Val Ser Trp Gly Asn Met Lys Leu Gln Asp Ser Ala Pro Cys Lys
    210                 215                 220

gaa ttc aaa aca act aag ttg att agc gac tta tgc acg gaa cct gtg      720
Glu Phe Lys Thr Thr Lys Leu Ile Ser Asp Leu Cys Thr Glu Pro Val
225                 230                 235                 240

tgc gct cag                                                          729
Cys Ala Gln


<210> SEQ ID NO 4
<211> LENGTH: 243
<212> TYPE: PRT
<213> ORGANISM: Papaya Leaf-Distortion Mosaic Virus

<400> SEQUENCE: 4
```

-continued

```
Gly Ala Ser Ser Val Lys Gly Leu Arg Asp Tyr Asn Gly Val Ala Ser
1               5                   10                  15

Ala Ile Cys Gln Leu Thr Asn Asn Ser Asn Gly Arg Ser Thr Thr Thr
            20                  25                  30

Tyr Gly Val Gly Phe Gly Ser Tyr Ile Ile Val Asn Arg His Leu Phe
        35                  40                  45

Lys Glu Asn Asn Gly Asn Leu Leu Ile Lys Ser Thr His Gly Asn Phe
    50                  55                  60

Asn Ile Arg Asn Ser Lys Gln Ile Lys Val Val Gly Val Glu Asp Arg
65                  70                  75                  80

Asp Ile Ala Ile Leu Gln Met Pro Lys Asp Phe Pro Pro Phe Ala Gln
                85                  90                  95

Arg Leu Arg Phe Arg Asn Pro Ile Val Gly Glu Ser Ile Cys Leu Val
            100                 105                 110

Gly Asn Thr Phe Gln Glu Lys Tyr Asn Ala Ser Ile Val Ser Glu Thr
        115                 120                 125

Ser Lys Thr Phe Pro Arg Val Glu Gly Ser Phe Trp Lys His Trp Ile
    130                 135                 140

Asn Thr Thr Glu Gly His Cys Gly Leu Pro Leu Val Ser Val Thr Asp
145                 150                 155                 160

Gly Phe Ile Val Gly Ile His Ser Leu Met Ser His Lys Tyr Asp His
                165                 170                 175

Asn Tyr Phe Ser Asn Phe Asp Asp Ala Phe Glu Gly Asp Tyr Ile Asn
            180                 185                 190

Lys Leu Lys Glu Leu Lys Trp Glu Gln Asn Trp Thr Tyr Asn Val Asn
        195                 200                 205

Thr Val Ser Trp Gly Asn Met Lys Leu Gln Asp Ser Ala Pro Cys Lys
    210                 215                 220

Glu Phe Lys Thr Thr Lys Leu Ile Ser Asp Leu Cys Thr Glu Pro Val
225                 230                 235                 240

Cys Ala Gln
```